United States Patent [19]

Adams et al.

[11] Patent Number: 5,525,608
[45] Date of Patent: Jun. 11, 1996

[54] 17B-ARYL-4-AZA-STEROID DERIVATIVES USEFUL AS 5-ALPHA-REDUCTASE INHIBITORS

[75] Inventors: Alan D. Adams, Piscataway; Gary H. Rasmusson, Watchung; Nathan G. Steinberg, Clark, all of N.J.

[73] Assignee: Merck & Co., Inc., Rahway, N.J.

[21] Appl. No.: 230,277

[22] Filed: Apr. 20, 1994

[51] Int. Cl.$^6$ .................................................. A61K 31/58
[52] U.S. Cl. ........................ 514/284; 546/77; 546/78
[58] Field of Search ........................ 514/284; 546/77, 546/78

[56] References Cited

U.S. PATENT DOCUMENTS

| | | | |
|---|---|---|---|
| 4,377,584 | 3/1983 | Rasmusson et al. | 514/284 |
| 4,760,071 | 7/1988 | Rasmusson et al. | 514/284 |
| 4,882,319 | 11/1989 | Holt et al. | 514/119 |
| 5,049,562 | 9/1991 | Rasmusson et al. | 514/284 |
| 5,061,802 | 10/1991 | Steinberg et al. | 546/77 |
| 5,098,908 | 3/1992 | Steinberg et al. | 514/284 |
| 5,151,430 | 9/1992 | Steinberg et al. | 514/284 |
| 5,162,332 | 11/1992 | Steinberg et al. | 514/284 |
| 5,175,155 | 12/1992 | Juniewicz et al. | 514/176 |
| 5,359,071 | 10/1994 | Durette et al. | 546/77 |

FOREIGN PATENT DOCUMENTS

| | | |
|---|---|---|
| WO92/16213 | 10/1992 | WIPO. |
| WO94/20104 | 9/1994 | WIPO. |

OTHER PUBLICATIONS

Helliker, Wall St. Journal, 7 Jun. 1991, pp. A1, A7.
Stinson, Chem & Eng News, 29 Jun. 1992, pp. 7–8.
A. Diani et al., "Hair Growth Effects of Oral Admin. of Finasteride, a Steroid 5 alpha–Reductase Inhibitor . . . ", J. Clin. Endocrin. Metab., vol. 74, 345–350 (1992).
Gormley et al., "Pharmaceutical combination for the treatment of prostatic hyperplasia, containing a 5alpha–reductase inhibitor and an alpha 1–adrenergic receptor blocker, and synthesis of some 5alpha–reductase inhibitors", Chem. Abstracts, vol. 118, No. 11, abstract 102309c (1993).
Gormley et al., "Pharmaceutical combination for the treatment of prostatic cancer containing a 5 alpha reductase inhibitor and an antiandrogen", Chem. Abstracts, vol. 118, No. 21, abstract 213352h (1993).
Back, "Oxidation of Azasteroid Lactams and Alcohols with Benzeneseleninic Anhydride", J. Org. Chem., vol. 46, pp. 1442–1446 (1981).

*Primary Examiner*—Donald G. Daus
*Attorney, Agent, or Firm*—Catherine D. Fitch; Carol S. Quagliato; Joanne M. Giesser

[57] ABSTRACT

Compounds of the formula

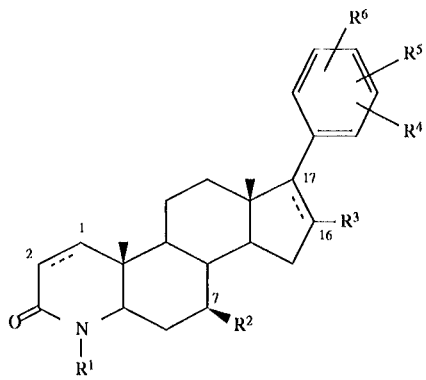

are inhibitors of 5α-reductase and are useful alone or in combination with other active agents for the treatment of hyperandrogenic disorders such as acne vulgaris, seborrhea, female hirsutism, male pattern baldness, and benign prostatic hyperplasia.

25 Claims, No Drawings

17β-ARYL-4-AZA-STEROID DERIVATIVES USEFUL AS 5-ALPHA-REDUCTASE INHIBITORS

FIELD OF THE INVENTION

The present invention provides novel compounds, novel compositions, methods of their use and methods of their manufacture, where such compounds are generally pharmacologically useful as agents in therapies whose mechanism of action rely on the inhibition of 5α-reductase, and more particularly, the inhibition of 5α-reductase isozyme type 1.

BACKGROUND OF THE INVENTION

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by an excessive accumulation of testosterone ("T") or similar androgenic hormones in the metabolic system. Androgenic alopecia is also known as androgenetic alopecia. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et all., *Endocrinol.* 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone ("DHT"), formed locally in the target organ by the action of 5α-reductase, which converts testosterone to DHT. Inhibitors of 5α-reductase will serve to prevent or lessen symptoms of hyperandrogenic stimulation in these organs. See especially U.S. Pat. Nos. 4,377,584, issued Mar. 22, 1983, and 4,760,071, issued Jul. 26, 1988, both assigned to Merck & Co., Inc. It is now known that a second 5α-reductase isozyme exists, which interacts with skin tissues, especially in scalp tissues. See, e.g., G. Harris, et al., *Proc. Natl. Acad. Sci. USA*, Vol. 89, pp. 10787–10791 (November 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

Since 5α-reductase and its isozymes convert testosterone to DHT, inhibition of either or both of the isozymes would serve to alleviate the conditions and diseases mediated by DHT. The present invention addresses this by providing novel compounds that are active as inhibitors of 5α-reductase type 1.

SUMMARY OF THE INVENTION

The novel compounds of the present invention are those of structural formula I:

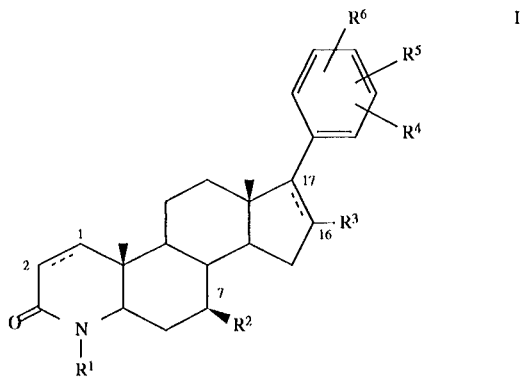

or a pharmaceutically acceptable salt or ester thereof, and are inhibitors of 5α-reductase, particularly 5α-reductase type 1. The compounds of formula I are useful in the oral, systemic, parenteral or topical treatment of hyperandrogenic conditions such as acne vulgaris, seborrhea, androgenic alopecia which includes female and male pattern baldness, female hirsutism, benign prostatic hyperplasia, and the treatment of prostatic carcinoma, as well as in the treatment of prostatitis. Furthermore, the compounds of formula I wherein the C16C–17 bond is a double bond are useful as intermediates in the preparation of compounds wherein the C16–C17 bond is saturated.

Therefore it is an object of this invention to provide compounds that have sufficient activity in the inhibition of 5α-reductase type 1. It is an additional object of this invention to provide methods of using the compounds of formula I for the treatment of hyperandrogenic conditions such as acne vulgaris, seborrhea, androgenic alopecia, male pattern baldness, female hirsutism, benign prostatic hyperplasia, and the treatment of prostatic carcinoma, as well as the treatment of prostatitis. It is a further object of this invention to provide pharmaceutical compositions for the compounds of formula I. Another object of this invention is to provide compounds of formula I in combination with other active agents, for example a 5α-reductase type 2 inhibitor, such as finasteride, or a potassium channel opener, such as minoxidil, or a retinoic acid or a derivative thereof, wherein such combinations would be useful in one or more of the abovementioned methods of treatment or pharmaceutical compositions.

DETAILED DESCRIPTION OF THE INVENTION

The novel compounds of this invention have the structural formula I:

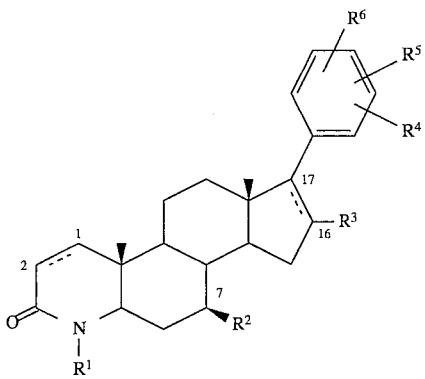

or a pharmaceutically acceptable salt or ester thereof, wherein: the C1–C2 bond and the C16–C 17 bond designated "======" each independently represent a single or double bond:

$R^1$ and $R^2$ are independently selected from:
1) —H,
2) —CH$_3$ and
3) —CH$_2$CH$_3$;

$R^3$ is selected from:
1) —H and
2) —CH$_3$; and $R^3$ is β-oriented if C16–C17 is saturated:

$R^4$, $R^5$ and $R^6$ are independently selected from:
1) —H,
2) —C$_{1-8}$ alkyl, unsubstituted or substituted with —OH,
3) —C$_{1-3}$ perfluoroalkyl,
4) —halo,
5) —OR$^7$, wherein R$^7$ is
  a) —H,
  b) —C$_{1-8}$ alkyl,
  c) —C1—6 alkylcarbonyl,
  d) —C1—6 alkylsulfonyl, or
  e) —C1—6 alkoxycarbonyl,
6) —NHR$^7$,
7) —NO$_2$,
8) —S(C$_{1-6}$ alkylcarbonyl),
9) —S(O)$_n$C$_{1-8}$ alkyl, wherein n is 0, 1 or 2,
10) —CO$_2$R$^8$ wherein R$^8$ is
  a) —H or
  b) —C$_{1-8}$ alkyl,
11) —C(O)R$^8$,
12) —C(O)N(R$^8$)$_2$,
13) —CN,
14) —C(R$^8$)$_2$OR$^7$,
15) —C(R$^8$)$_2$NR$^7$,
16) —C(R$^8$)$_2$S(C$_{1-8}$ alkyl),
17) —C(R$^8$)$_2$S(C$_{1-6}$ alkylcarbonyl), and
18) phenyl, unsubstituted or having 1 to 3 substituents selected from:
  a) —OH,
  b) halo,
  C) C$_{1-3}$ alkyl, and
  d) C$_{1-3}$ alkoxy; or $R^4$ and $R^5$ or $R^5$ and $R^6$, on vicinal carbon atoms, may be joined to form with the phenyl to which they are attached a naphthyl or indanyl group; and the 17-position substituent is β-oriented if C16–17 is saturated.

Combinations of substituents and/or variables are permissable only if such combinations result in stable compounds.

In one embodiment of the instant invention are compounds of formula I having structural formula II:

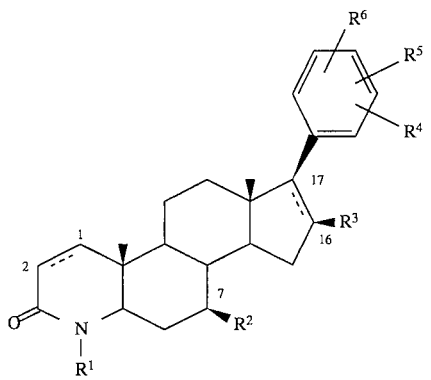

or a pharmaceutically acceptable salt or ester thereof.

In one class of this embodiment are compounds of formula III

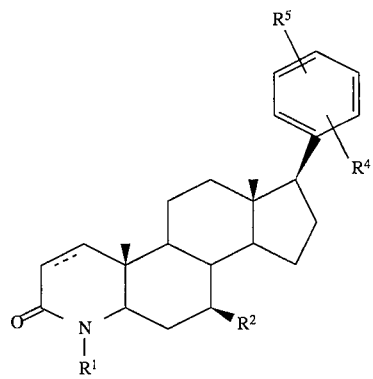

or a pharmaceutically acceptable salt or ester thereof, wherein:

$R^1$ is —H or —CH$_3$; and $R^2$ is —CH$_3$ or —CH$_2$CH$_3$; and $R^4$ and $R^5$ are as defined above in Formula I.

In a second embodiment of the instant invention are compounds of formula I having structural formula IV:

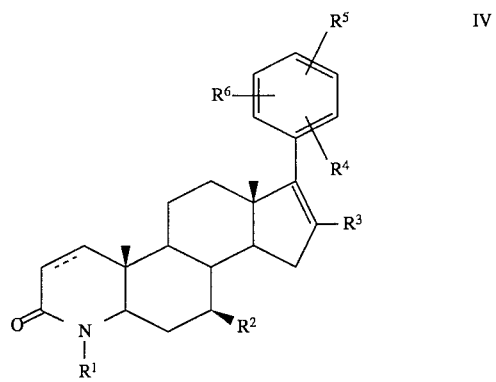

or a pharmaceutically acceptable salt or ester thereof.

In one class of this second embodiment are compounds of formula V

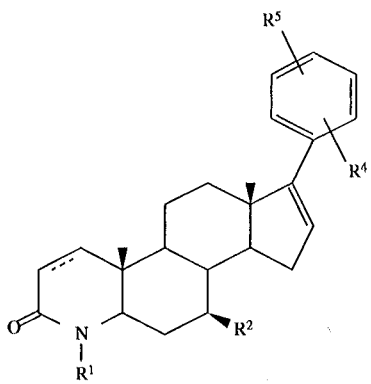

or a pharmaceutically acceptable salt or ester thereof, wherein:

$R^1$ is —H or —CH$_3$; and $R^2$ is —CH$_3$ or —CH$_2$CH$_3$; and $R^4$ and $R^5$ are as defined above in Formula I.

In one sub-class of this invention are compounds of either formula III or formula V further limited to those wherein:

$R^1$ is —H or —CH$_3$;

$R^2$ is —CH$_3$; and $R^4$ and $R^5$ are independently selected from a) —H,
b) —OH,
c) —CH$_3$,
d) —OCH$_3$,
e) —S(O)$_n$—CH$_3$,
f) —CF$_3$,
g) halo,
h) —CHO,
i) CN,
j) —NHR$^7$, or $R^4$ and $R^5$ are on vicinal carbon atoms and are joined to form with the phenyl to which they are attached a naphthyl group.

In a second sub-class of this invention are compounds of either formula III or formula V further limited to those wherein: the C1–C2 bond is a single bond; $R^1$ is —H or —CH$_3$; and $R^2$ is —CH$_3$.

Within this second sub-class are compounds of formula either III or formula V still further limited to those wherein $R^4$ and $R^5$ are independently selected from:

a) —H,
b) —OH,
c) —CH$_3$,
d) —OCH$_3$,
e) —S(O)$_n$—CH$_3$,
f) —CF$_3$,
g) halo,
h) —CHO,
i) CN,
j) —NHR$^7$, or $R^4$ and $R^5$ are on vicinal carbon atoms and are joined to form with the phenyl to which they are attached a naphthyl group.

Examples of compounds within this second sub-class are those in the following table:

| $R^1$ | $R^2$ | |
|---|---|---|
| —CH$_3$ | —CH$_3$ | phenyl |
| —CH$_3$ | —CH$_3$ | 4-methylthiophenyl |
| —CH$_3$ | —CH$_3$ | 4-chlorophenyl |
| —CH$_3$ | —CH$_3$ | 3,5-bis(trifluoromethyl)-phenyl |
| —CH$_3$ | —CH$_3$ | 3,5-dichlorophenyl |
| —CH$_3$ | —CH$_3$ | 1-naphthyl |
| —CH$_3$ | —CH$_3$ | 2-methoxyphenyl |
| —CH$_3$ | —CH$_3$ | 3-methoxyphenyl |
| —CH$_3$ | —CH$_3$ | 4-methoxyphenyl |
| —CH$_3$ | —CH$_3$ | 4-methylsulfonylphenyl |
| —CH$_3$ | —CH$_3$ | 3-aminophenyl |
| —CH$_3$ | —CH$_3$ | 3-(carbethoxyamino)-phenyl |

Additionally, novel compounds of the present invention include but are not limited to those described in the Examples below, and Tables I and II, below, and corresponding analogs wherein the C1–C2 bond is saturated or unsaturated as appropriate.

As used herein "alkyl" is intended to include both branched- and straight-chain saturated aliphatic hydrocarbon groups having the specified number of carbon atoms, e.g., methyl (Me), ethyl (Et), propyl, butyl, iso-propyl (i-Pr), iso-butyl (i-Bu), sec-butyl (s-Bu), ten-butyl (t-Bu) cyclopropyl, cyclopentyl and cyclohexyl. "Alkyloxy" (or "alkoxy") represents an alkyl group having the indicated number of carbon atoms attached through an oxygen bridge, e.g., methoxy, ethoxy, propyloxy, iso-propoxy, n-butoxy, iso-butoxy, sec-butoxy, t-butoxy and the like.

The term halo or halogen is meant to include fluoro, chloro, bromo and iodo.

Unless otherwise indicated the 17-position substituent and any 16-position substituent are assumed to be in the beta configuration when C16–C17 is saturated.

Also included within the scope of this invention are pharmaceutically acceptable salts of the compounds of formula I, where a basic or acidic group is present on the structure. When an acidic substituent is present, i.e. —COOH, there can be formed the ammonium, sodium, potassium, calcium salt, and the like, for use as the dosage form. Where a basic group is present, such as amino, an acidic salt, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Representative salts include the following salts: acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tanrate, hydroxynaphthoate, teoclate, iodide, tosylate, isothionate, triethiodide, lactate, and valerate.

The compounds of the present invention are chiral. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "therapeutically effective amount" shall mean that amount of a drug or pharmaceutical agent that will elicit the biological or medical response of a tissue, system, animal or human that is being sought by a researcher, veterinarian, medical doctor or other clinician, which includes alleviation of the symptoms of the disease being treated. The term "mammal" includes humans.

The present invention has the objective of providing s methods of treating hyperandrogenic conditions including androgenic alopecia, male pattern baldness, acne vulgaris, seborrhea, and female hirsutism by oral, systemic, parenteral or topical administration of the novel compounds of formula I either alone or in combination with a 5α-reductase 2 inhibitor and/or a potassium channel opener. The term "treating androgenic alopecia" is intended to include the arresting and/or reversing of androgenic alopecia, and the promotion of hair growth. The present invention has the further objective of providing methods of treating benign prostatic hyperplasia, prostatitis, and treating and/or preventing prostatic carcinoma by oral, systemic or parenteral administration of the novel compounds of formula I either alone or in combination with a 5α-reductase 2 inhibitor.

The present invention also has the objective of providing suitable topical, oral, systemic and parenteral pharmaceutical formulations for use in the novel methods of treatment of the present invention. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an antiandrogenic agent.

The daily dosage of the products may be varied over a wide range from 0.01 to 1,000 mg per adult human/per day. For oral administration, the compositions are preferably provided in the form of tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg./kg. to about 50 mg./kg. of body weight per day. The range is more particularly from about 0.001 mg./kg. to 7 mg./kg. of body weight per day.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment of androgenic alopecia, male pattern baldness, acne vulgaris, seborrhea, and female hirsutism, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. These topical pharmaceutical compositions containing the compounds of the present invention ordinarily include about 0.005% to 5% by weight of the active compound in admixture with a pharmaceutically acceptable vehicle.

For the treatment of acne vulgaris, androgenic alopecia, male pattern baldness, seborrhea, female hirsutism, benign prostatic treatment of prostatic cancer, the compounds of the instant invention can be combined with a therapeutically effective amount of another 5α-reductase inhibitor, such as finasteride, or other 5α-reductase inhibitor compounds having type 2 activity or dual activity for both isozymes, in a single oral, systemic, or parenteral pharmaceutical dosage formulation. Alternatively, a combined therapy can be employed wherein the compound of formula I and the other 5α-reductase inhibitor are administered in separate oral, systemic, or parenteral dosage formulations. Also, for the skin and scalp related disorders of acne vulgaris, androgenic alopecia, male pattern baldness, seborrhea, and female hirsutism, the compounds of the instant invention and another 5α-reductase inhibitor such as finasteride can be formulated for topical administration. For example, a compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of formula I. See, e.g., U.S. Pat. Nos. 4,377,584 and 4,760,071 which describe dosages and formulations for 5α-reductase inhibitors.

Furthermore, administration of a compound of the present invention in combination with a therapeutically effective amount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, may be used for the treatment of androgenic alopecia including male pattern baldness. Therapy may further comprise the administration of a 5α-reductase type 2 inhibitor such as finasteride, or a type 1 and type 2 dual inhibitor, in combination with a compound of the present invention and a potassium channel opener such as minoxidil. The active agents can be administered in a single topical dosage formulation, or each active agent can be administered in a separate dosage formulation, e.g., in separate topical dosage formulations, or an oral dosage formulation of a compound of formula I in combination with a topical dosage formulation of, e.g., minoxidil, or a single oral dosage formulation of a compound of formula I and another 5α-reductase inhibitor, in combination with a topical dosage formulation of, e.g., minoxidil. See, e.g., U.S. Pat. Nos. 4,596,812, 4,139,619 and WO 92/02225, published 20 Feb. 1992, for dosages and formulations of calcium channel openers.

Furthermore, for the treatment of acne vulgaris, a combined therapy can be used by administering a therapeutically effective amount of a compound of formula I in combination with a therapeutically effective amount of retinoic acid or a derivative thereof, e.g. an ester or amide derivative thereof, such as e.g., tretinoin or isotretinoin.

Also, for the treatment of benign prostatic hyperplasia, a combined therapy comprising a administration of a compound of formula I with a 5α-reductase type 2 inhibitor, such as e.g. finasteride, and an alpha-1 adrenergic receptor antagonist, such as e.g. terazosin, doxazosin, prazosin, bunazosin, indoramin or alfuzosin, may be employed. More particularly, the combined therapy can comprise administering a compound of formula I with a 5α-reductase type 2 inhibitor, such as e.g. finasteride, and an alpha-$1_c$ adrenergic receptor antagonist. Compounds which are useful as alpha-$1_c$ adrenergic receptor antagonists can be identified according to the procedures described in PCT/US93/09187 (WO94/08040, published Apr. 14, 1994).

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

SCHEME I

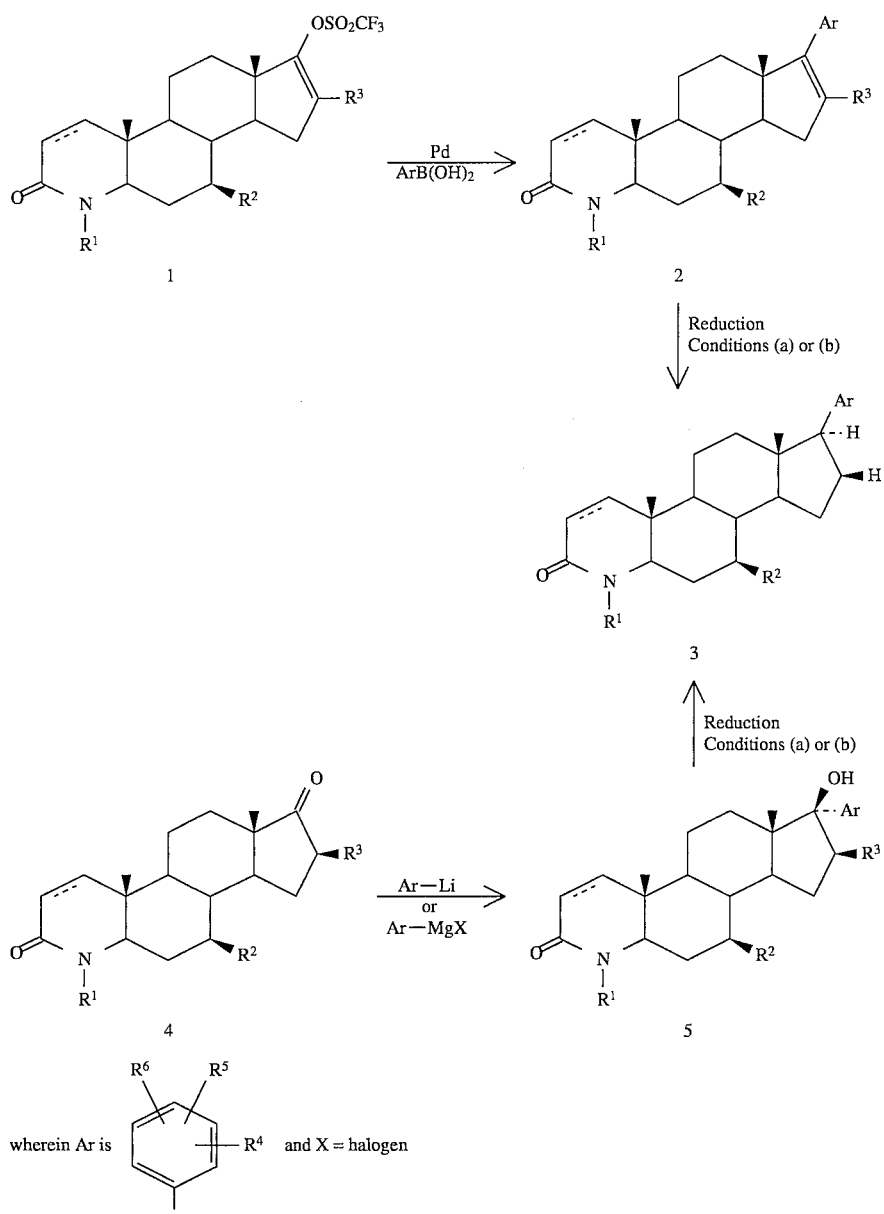

Reduction Conditions (a) Pd or Pt and $H_2$
(b) $Et_3SiH$, $CF_3CO_2H$

The starting materials 1 in Scheme I are readily prepared from the corresponding 3,17-diones by treatment with potassium hexamethyldisilazide (also known as potassium bis(trimethylsilyl)amide) and N-phenyltrifluoromethane-sulfonimide as described in Example 1, Step A, or for starting materials where $R^1$ is —H, by treatment with trifluoromethanesulfonic anhydride as described in Example 14.

The next step in Scheme I, the catalysed coupling of an aryl boronic acid to 1 to form 2, is a novel process embodiment of this invention. In this process, a mixture of the aryl boronic acid, tetrakis-(triphenylphosphine)palladium, lithium chloride and the 17-trifluoromethanesulfonyloxy compound 1 in a mixture of an aromatic solvent such as benzene or toluene and a $C_{1-3}$ alkanol, especially ethanol, is refluxed with aqueous sodium carbonate.

Another novel process embodiment of this invention is the catalytic reduction of the $\Delta^1$ (if present) and the $\Delta^{16}$ double bonds with a noble metal catalyst such as palladium on carbon in a $C_{1-3}$ lower alkanol, especially ethanol. The reaction proceeds readily at room temperature and pressure, but temperatures as low as about 10° C. and as high as reflux temperature can be employed. Similarly, higher pressures up to about 25 psi may be employed.

Certain $\Delta16$-compounds resist catalytic hydrogenation or give unwanted by-products. In some of these cases ionic reduction affords the desired materials. An example of ionic reduction is described in Example 4.

A third novel process of this embodiment, arylation of 4 to give 5 followed by reduction to 3 comprises treating the androstane-3,17-dione with an aryl lithium in an aprotic solvent at about −100° C. to about −60° C., especially about −78° C. to give the 17-hydroxy- 17-aryl intermediate 5.

The 17-OH group is eliminated by reduction with a noble metal catalyst such as palladium in an organic carboxylic acid such as acetic or propionic acid at or about normal temperature and pressure.

The arylboronic acids used in the novel processes are generally commercially available. Those that are not commercially available may be prepared by a process substantially as described in Example 3 below.

SCHEME 2

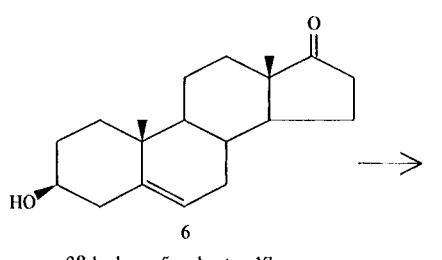

6
3β-hydroxy-5-androsten-17-one

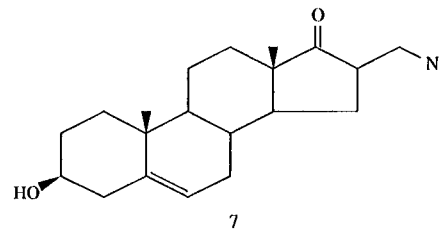

7

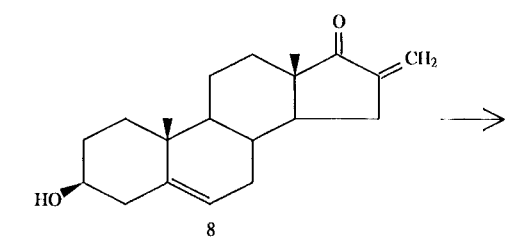

8

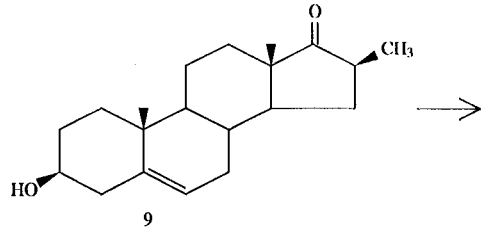

9

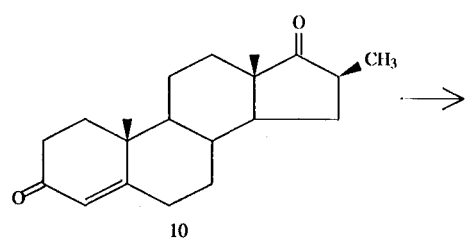

10

-continued
SCHEME 2

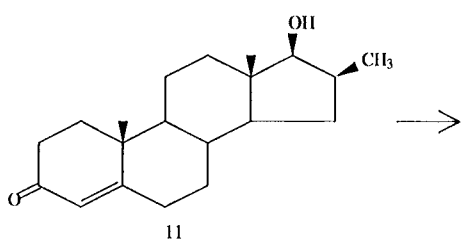

11

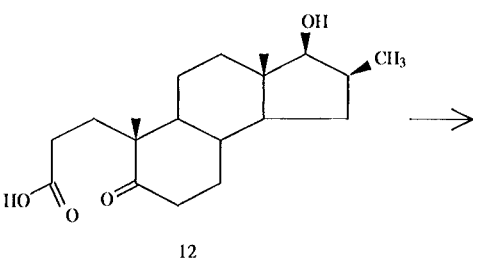

12

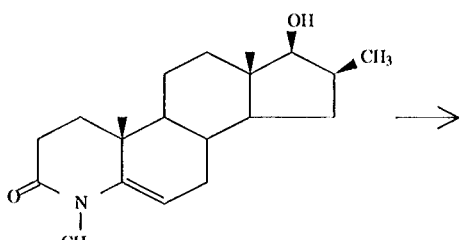

13

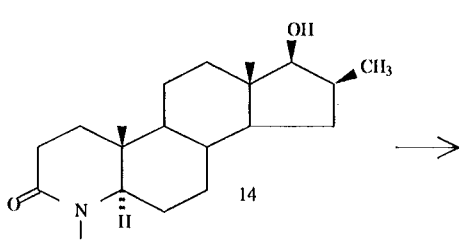

14

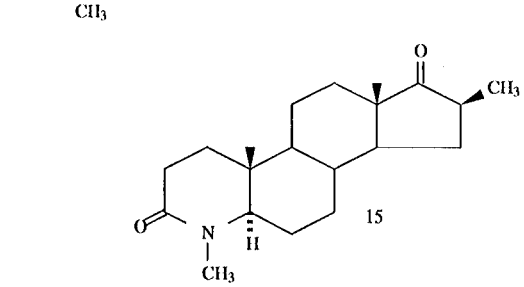

15

The 3,17-dione starting materials can be made by procedures known in the art. For example, compound 15 can be made according to the following procedures as exemplified in Scheme 2.

Following the procedure in *JACS*, Vol. 70, p. 3872 (1948), 6 is reacted via a Mannich reaction with paraformaldehyde and dry dimethylamine hydrochloride in isoamyl alcohol under reflux for two hours to produce the 16-dimethylaminomethyl derivative 7. This in turn is treated by the procedure in *JACS*, 77, p. 5677 (1955) via steam distillation to yield the 20-methylene analog 8, which is catalytically hydrogenated selectively from the alpha face at C-16 using 10% Pd/C catalyst in methanol solvent at room temperature under hydrogen balloon pressure for about 5–10 minutes to yield primarily the 16-beta-methyl derivative 9. This is treated under Oppenauer oxidation conditions using aluminum isopropoxide, cyclohexanone, in dry toluene solvent under reflux for 2–4 hours, azeotropically removing water to yield after chromatographic separation the 4-en-3-one derivative 10. The 3- and 17-keto groups in 10 are reduced by treating with 25% DIBAL (diisobutylaluminum hydride) in toluene followed by in situ Oppenauer oxidation of the 3-ol to the 3-one with acetone and 2-propanol at 0° C. for about 6 hours to yield 11 (see also the procedure in *Berichte*, Vol. 109, p. 2954, (1976)). The seco acid 12 is produced by oxidizing 11 with a mixture of sodium periodate, potassium permanganate, sodium carbonate, water, t-butanol at reflux for one hour. (See also the procedure in *J. Med. Chem.*, Vol. 27, p. 1690, (1984)). The seco acid 12 is then treated with methylamine hydrochloride, sodium acetate in ethylene glycol at 180° C. for 8 hours to produce the 4-N-methyl analog 13. The 5-ene 13 is catalytically hydrogenated using $PtO_2$ catalyst in glacial acetic acid at 60° C. in a hydrogen atmosphere to yield the 17β-hydroxy-5α analog 14. The 17-keto compound 15 is made by oxidizing the 17-hydroxy compound 14 with a mixture of TPAP (tetrapropylammonium perruthenate), N-methyl morpholine-N-oxide, 4 Å molecular sieves in methylene chloride at 0° C. for about one hour.

The starting material 4-aza-4-methyl-5α-androstan-3,17-dione can be made according to the methods described in Rasmusson, et al.,*J. Med. Chem.*,27, p. 1690–1701 (1984). The synthesis of other 4-aza- 5α-androstan-3,17-dione starting materials are described in Examples 15 and 16, below.

All temperatures given in the following examples are in degrees Celsius. Some abbreviations used herein are as follows: "BSTFA" is bis(trimethylsilyl)trifluoroacetamide; "DDQ" is 2,3-dichloro- 5,6-dicyano-1,4-benzoquinone; "DMF" is dimethylformamide; "EtOAc" is ethyl acetate; "TBDMS" is t-butyldimethylsilyl; "Tf" is $-SO_2CF_3$; "TFA" is trifluoroacetic acid; "THF" is tetrahydrofuran, Triflic acid is trifluoromethanesulfonic acid.

EXAMPLE 1

Preparation of 4,7β-dimethyl-17β-phenyl-4-aza-5α-androst-3-one

Step A:

Preparation of 4,7β-dimethyl-17-(trifluoromethylsulfonyloxy)- 4-aza-5α-androst-16-en-3-one A solution of 1.0 g (3.15 mmol) of 4,7β-dimethyl-4-aza-5α-androstane-3,17-dione in 10 ml of tetrahydrofuran (THF) was treated dropwise at 0° C. with 7.3 ml of a 0.5M solution of potassium hexamethyldisilazide in toluene. After 30 min. at 0° C. the mixture was treated with 1.35 g of N-phenyl-trifluoromethanesulfonimide and the resulting clear solution was stirred for 30 min. Aqueous ammonium chloride solution and ethyl acetate were added and mixed well. The organic layer was washed with 1N HCl, water, 1N $NaHCO_3$, and saturated NaCl solution resp. The organic layer was dried and concentrated to give the crude product. Chromatography on silica gel eluted with 5:1 hexane: isopropanol afforded the title compound as a heavy oil which crystallized slowly on storage at 5° C.

Step B:

Preparation of 4,7β-dimethyl-17-phenyl-4-aza-5α-androst- 16-en-3-one

Phenylboronic acid (111 mg, 0.91 mmol, 2 eq.), tetrakis-(triphenylphosphine)-palladium (26.3 rag, 0.02 mmol, 0.05 e.g.), lithium chloride (77 mg, 1.8 mmol, 4 eq.) and 4,7β-dimethyl-17-trifluoromethanesulfonyloxy- 4-aza-5α-androst-16-en-3-one (204 mg, 0.45 mmol, 1.0 eq.) were combined in 7 ml of toluene and 3 ml ethanol. Aqueous 2M sodium carbonate (1 ml, 2 mmol) was added, and the mixture heated to reflux. When the steroid starting material was consumed, the mixture was cooled to room temperature, diluted with ethyl acetate and water, and the phases separated. The organic phase was washed again with dilute aq. sodium carbonate, followed by saturated aq. $NH_4Cl$. The organic phase was dried and reduced in vacuo. The mixture was purified by chromatography on $SiO_2$ (10 g), eluting with hexanes:acetone 4:1, to give the desired product as an oil.

Step C:

Preparation of 4,7β-dimethyl-17β-phenyl-4-aza-5α-androstan- 3-one

The 4,7β-dimethyl-17-phenyl-4-aza-5α-androst-16-en-3-one (113 mg) was dissolved in 10 ml of ethanol with 48 mg of 10% palladium on activated carbon. The flask was purged three times, vacuum versus hydrogen, and stirred vigorously under slight hydrogen pressure at room temperature until starting material was consumed. (Hydrogen pressure is maintained by an attached balloon.) The solution was filtered through celite and reduced in vacuo. The title compound, after elution through 12 g of silica gel with 5:1 hexane:isopropanol, was isolated by crystallization from ethyl ether to give the title compound.

EXAMPLE 2

Step A:

Preparation of 17β-hydroxy-17α-phenyl-4-aza-5α-androstan-3-one

To a stirred, room temperature suspension of 4-aza-5α-androstane- 3,17-dione (2.0 g) in 265 ml of tetrahydrofuran was added 3.7 ml of 1.8M phenyl lithium in cyclohexane/ether (70:30). After stirring for 45 min. the reaction mixture was cooled in an acetone-Dry Ice bath and 22.4 ml of additional phenyl lithium solution was added. The temperature was held at −78° C. for 6 hr. and then at −30° C. for 16 hr. The solution was warmed to −10° C. and quenched by addition of 10% aqueous $NH_4Cl$ solution. The organic layer was separated and combined with an ethyl acetate layer from the extraction of the aqueous layer. The organic layer was washed with water, dried and concentrated to leave the crude product. Chromatography on silica gel (340 ml solid volume) eluted with 9:1 ethyl acetate/methanol gave early fractions containing the pure title product. Subsequent fractions contained mixtures of starting material with the title compound from which additional product could be obtained on rechromatography.

Step B:

Preparation of 17β-phenyl-4-aza-5α-androstan-3-one

A mixture of 17β-hydroxy-17α-phenyl-4-aza-5α-androstan- 3-one (93 mg) and 30% Pd/C catalyst (100 mg) in 3.0 ml of glacial acetic acid was stirred at 60° C. under balloon pressure of hydrogen gas for 5.5 hr. The catalyst was removed and the solution concentrated to a gummy residue. Crystallization from ethyl acetate gave the title product. The mother liquors contained additional desired product which could be recovered by HPLC on silica gel eluted with 9:1 dichloromethane/isopropanol.

EXAMPLE 3

Preparation of 2-Methoxyphenylboronic acid

To a stirred, cold (−78° C.) solution of 2-iodoanisole (2.85 ml, 5.6 g) in 50 ml of tetrahydrofuran under nitrogen was added 10.0 ml of 2.5M n-butyl lithium in hexane. After 15 min. triisopropyl borate (3.38 ml, 4.7 g) was added and the reaction was allowed to come to and remain at room temperature for 1.5 hr. The mixture was poured into an excess of 2N hydrochloric acid and diethyl ether was added. The resulting mixture was stirred vigorously for 30 min. and the phases were separated. The ether layer was washed with aqueous sodium bisulfite until colorless and then with saturated sodium chloride solution and then dried over magnesium sulfate. Concentration of the ether layer gave the crude boronic acid which crystallized from ether to give the title product.

EXAMPLE 4

Preparation of 4-Methyl-17β-(4-methylthiophenyl)-4-aza-5α-androstan-3-one

A solution of 4-methyl-17β-(4-methylthiophenyl)-4-aza-5α-androst-16-en-3-one (50.6 mg) and 0.17 ml of triethylsilane in 5.0 ml of dichloromethane was treated at room temperature dropwise with 300 μl of trifluoroacetic acid and was allowed to stand for 16 hr. Additional dichloromethane and 15 ml of saturated aqueous NaHCO₃ solution was added with stirring. The organic layer was worked up to leave a residue which was crystallized from ethyl acetate to give the title product.

EXAMPLE 5

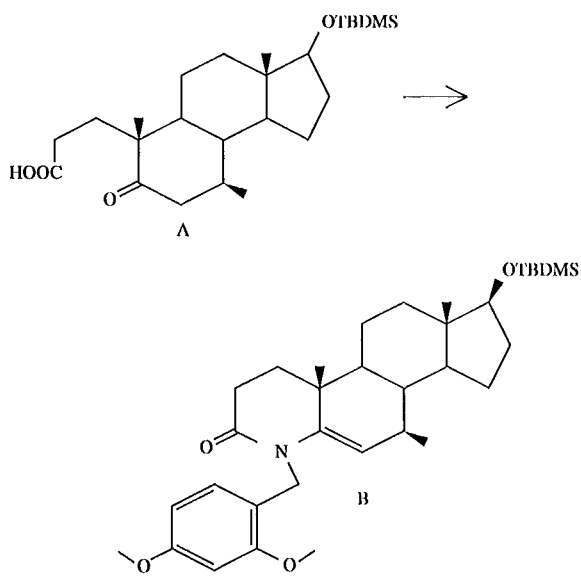

Preparation of 17β-(t-butyldimethylsilyloxy)-4-(2,4-dimethoxybenzyl)-7β-methyl-4-aza-5-androsten-3-one (B)

Seco acid (A) (300 gm) was dissolved in 8,699 ml of xylenes and to this was added 173.1 gm of 2,4-dimethoxybenzylamine hydrochloride and 69.14 gm of sodium acetate. The reaction was heated to reflux and maintained for 7 hrs. The reaction was diluted with 7.5 liters of water, the layers separated and the aqueous phase extracted once with EtOAc. The combined organic layers were washed with sat'd brine, dried over MgSO₄, and filtered through Na₂SO₄/charcoal and evaporated to a dark oil.

Chromatography on 5.0 Kg silica gel, packed in CH₂Cl₂ and eluted with 20% EtOAc/Hexane gave the title compound.

EXAMPLE 6

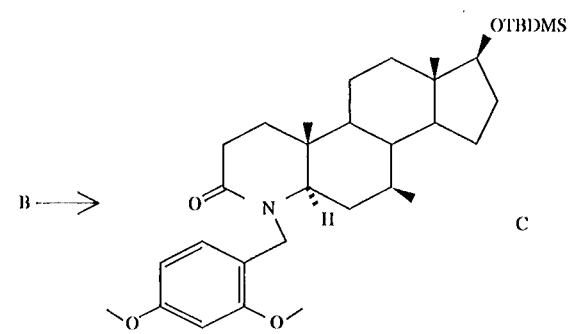

Preparation of 17β-(t-butyldimethylsilyloxy)-4-(2,4-dimethoxybenzyl)-7β-methyl-4-aza-5α-androstan-3-one(C)

Steroid (B) (227.9 gm) was dissolved in 2,125 ml of acetic acid, 24.5 gm of platinum oxide was added and the mixture was hydrogenated at 40 psi. at room temp. overnight. The reaction was filtered through solka flock and evaporated to an oil which was dissolved in ethyl acetate. The solution was washed twice with saturated brine, dried over MgSO₄ filtered through Na₂SO₄ and evaporated to a thick oil. TLC (thin layer chromatography) and proton NMR show about 25% starting material remains. The hydrogenation was repeated under the same conditions. After work-up the product's proton NMR was in accord with desired structure (C).

EXAMPLE 7

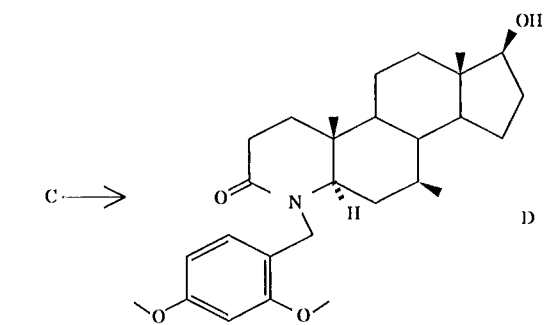

Preparation of 4-(2,4-dimethoxybenzyl)-17β-hydroxy-7β-methyl-4-aza-5α-androstan-3-one (D)

Steroid (C) (190.8 gm) was dissolved in 3,482 mls of acetonitrile and treated with 174.1 mls of 48% aq. HF and stirred at room temp. overnight. The reaction was quenched with 200 ml of 10% sodium carbonate and concentrated to remove the acetonitrile. The separated product was taken up in ethyl acetate and washed with saturated brine, dried over MgSO$_4$, filtered through Na$_2$SO$_4$ and evaporated to a white solid. The proton NMR was in accord with desired structure (D).

EXAMPLE 8

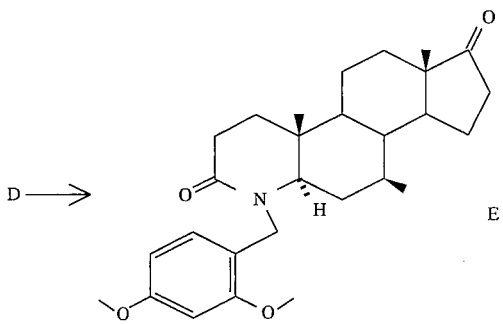

Preparation of 4-(2,4-dimethoxybenzyl)-7β-methyl-4-aza-5α-androstan-3,17-dione (E)

Hydroxy steroid (D) (135 gm) was dissolved in 1,621 mls of methylene chloride, treated with 135 gm of powdered sieves, cooled to 5° C. and treated with 51.9 gm of 4-methyl morpholine N-oxide followed by 5.0 gm of tetrapropylammonium perruthenate. The reaction was warmed to 23° C. and stirred for 2.5 hrs. The reaction was eluted through 1000 ml of silica gel with methylene chloride until the filtrate was colorless. Evaporation left a white foam. Chromatography on 10/1 ratio of silica gel packed in methylene chloride and elution with 50% EtOAc/Hexane to remove lead spot, then with 100% EtOAc to afford the product (E). The proton NMR was in accord with desired structure.

EXAMPLE 9

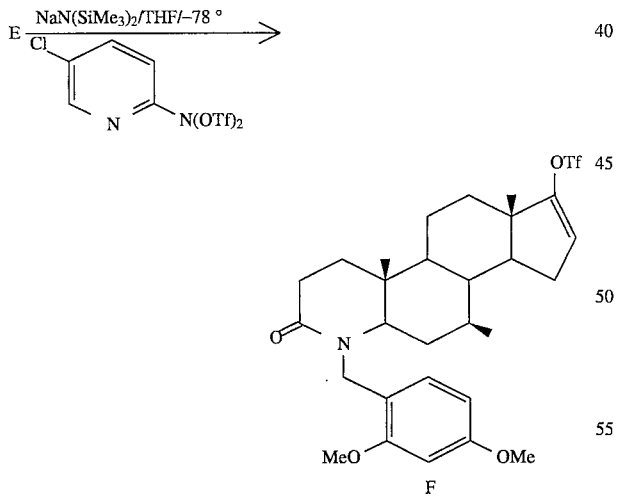

Synthesis of 17-trifluoromethanesulfonate-4-(2,4-dimethoxybenzyl)-7β-methyl-4-aza-5α-androst-16-en-3-one (F)

To a solution of 4-(2,4-dimethoxybenzyl)-7β-methyl-4-aza-5α-androstan-3,17-dione (4 g, 8.75 mmol) in THF (40 ml) at −78° was added slowly dropwise a solution of sodium bis(trimethylsilyl)amide (17.5 ml of 1.0M solution, 17.5 mmol). After stirring the reaction mixture for 15 minutes, a solution of 2-[N,N-bis(trifluoromethylsulfonyl)amino]-5-chloropyridine (6.84 g, 17.4 mmol) in THF (10 ml) was added. The reaction mixture was further stirred at −78° for 3 hrs and reaction quenched with aq. ammonium chloride. The reaction mixture was concentrated under vacuum, and partitioned between ethyl acetate and water. The organic layer was washed with aq. NaOH, brine, dried and concentrated. The residue was purified by chromatography over silica gel (5% acetone/methylene chloride) to give the title product. Mass spec. (MS) M$^+$ calculated 585; observed 586 (m+1). 1H NMR (400 MHz, CDCl$_3$, Key peaks) 0.89 (d, C-7), 0.91 (C-19), 0.94 (C-18), 3.07 (dd, C-5H), 3.77, 3.79 (OMe), 4.41, 4.83 (CH$_2$Ph), 5.52 (C-16H), 6.4, 6.99 (Ar).

EXAMPLE 10

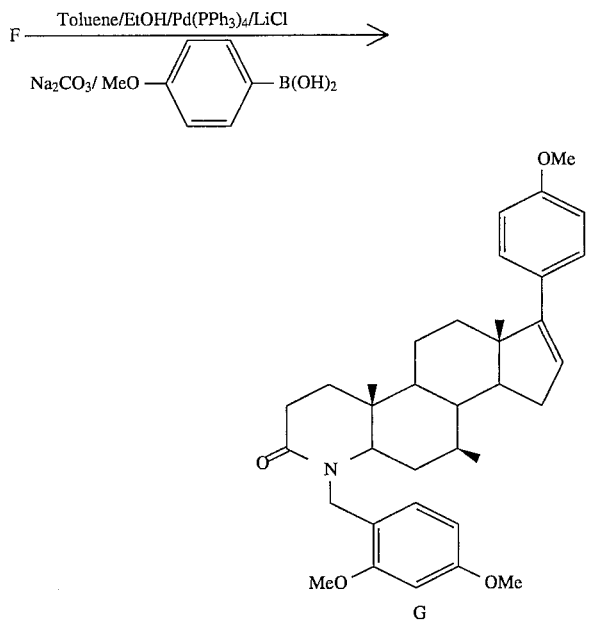

Synthesis of 17-(4-methoxyphenyl)-4-(2,4-dimethoxybenzyl)-7β-methyl- 4-aza-5α-androst-16-en-3-one (G)

To a solution of triflate (F) (1.178 g, 2 mmol) in toluene/ethanol (7:3, 40 ml) was added Pd(PPh$_3$)$_4$ (155.4 mg, 0.1 mmol), LiCl (339.12 mg, 8 mmol), 4-methoxyphenylboronic acid (492 mg, 3.5 mmol) and 4 ml of 2M aq. sodium carbonate. After stirring the reaction mixture at 120° (bath temp.) for 1.5 hr, the reaction mixture was cooled to 23°, diluted with ethyl acetate and organic layer was washed with aq. NH$_4$Cl, brine, dried and concentrated. The residue was purified by chromatography over silica gel (5% acetone in methylene chloride) to give the title product. Mass spec. (MS) M$^+$ calculated 543; observed 544 (m+1). $^1$H NMR (400 MHz, CDCl$_3$, Key peaks) 0.94 (C-19), 0.949 ( C-7, d, J=6.02), 0.995 (C-18), 3.1 (C-5), 3.79 and 3.796 (OMe), 4.48 and 4.85 (CH$_2$Ph), 5.76 (t, 16-H), 6.44, 6.84, 7.01, 7.26 (Ar).

EXAMPLE 11

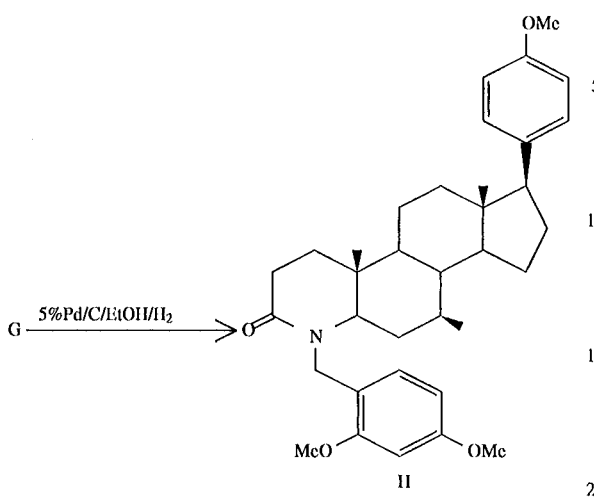

Synthesis of
17β-(4-methoxyphenyl)-4-(2,4-dimethoxybenzyl)-
7β-methyl- 4-aza-5α-androstan-3-one (H)

To a solution 17-(4-methoxyphenyl)-4-(2,4-dimethoxybenzyl)- 7β-methyl-4-aza-5α-androst-16-en-3-one (G) (750 mg, 1.38 mol) in ethanol (100 ml) was added 5% Pd/C (150 mg). The reaction mixture was evacuated and flushed with $H_2$ (3 times). After stirring the reaction mixture under $H_2$ atmosphere for 24 hrs, the reaction mixture was flushed with nitrogen, filtered and concentrated to give the product. Mass spec. (MS) M+ calculated 545; observed 546 (m+1). $^1H$ NMR (400 MHz, $CDCl_3$, Key peaks) 0.45 (C-18), 0.88 (C-19), 0.96 (C-7), 2.51 (t, C-17H), 3.1 (C-5), 3.78, 3.79, 3.80 (OMe), 4.43, 4.85 ($CH_2Ph$), 6.45, 6.82, 7.06, 7.1 (Ar).

EXAMPLE 12

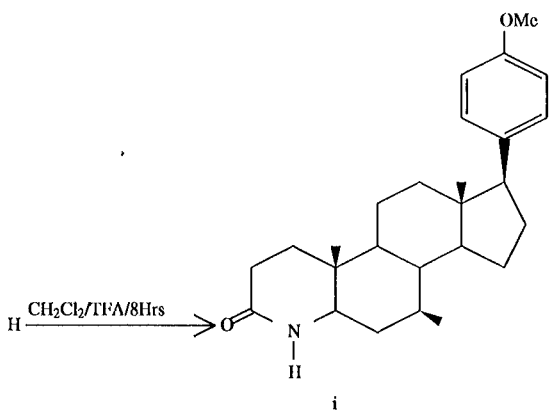

Synthesis of
17β-(4-methoxyphenyl)-7β-methyl-4-aza-5α-androstan-3-one (i)

To a solution of 17β-(4-methoxyphenyl)-4-(2,4-dimethoxybenzyl)- 7β-methyl-4-aza-5α-androstan-3-one (H) (725 mg, 1.33 mmol) in methylene chloride (15 ml) was added TFA (4 ml). After stirring the reaction mixture for 8 hrs at 23°, the reaction was quenched by addition of aq. $Na_2CO_3$ and partitioned between methylene chloride and aq. $Na_2CO_3$. The organic layer was washed with brine, dried and concentrated. The residue was purified over silica gel (10% acetone in methylene chloride) to give pure product. Mass spec. (MS) M+ calculated 395; observed 396 (m+1).

EXAMPLE 13

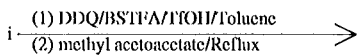

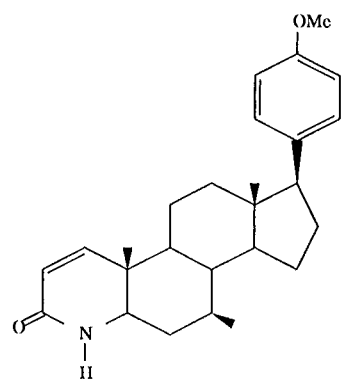

Synthesis of
17β-(4-methoxyphenyl)-7β-methyl-4-aza-5α-androst-1-en-3-one (J)

To a solution of 17β-(4-methoxyphenyl)-7β-methyl-4-aza-5α-androstan-3-one (i) (150 mg, 0.379 mmol) in toluene (3 ml) was added BSTFA (388 mg, 1.51 mmol), triflic acid (1 drop) and DDQ (97.38 mg, 0.429 mmol). After stirring the reaction mixture for 24 hrs at 23°, methyl acetoacetate (4.98 mg, 0.0429 mmol) was added and reaction mixture stirred for 1 hr at 23° and 24 hrs at 120° (bath temp.). The reaction mixture was cooled to room temperature, diluted with ethyl acetate, washed with aq. $Na_2CO_3$, aq. sodium bisulfite, dried and concentrated under vacuum. The residue was purified by HPLC (Silica gel semi prep. column) using 5% isopropanol/n-hexane as solvent to obtain the title compound. Mass spec. (MS) M+ calculated 393; observed 394 (m+1).

EXAMPLE 14

Preparation of
17-(trifluoromethylsulfonyloxy)-4-aza-5α-androst-16-en-3-one

Trifluoromethanesulfonic anhydride (80 μl, 0.47 mmol) was added at 25° C. to a solution of 145.2 mg of 4-aza-5α-androstane- 3,17-dione in 2.5 ml of methylene chloride. After 20 hr the mixture was added to saturated $NaHCO_3$ solution with stirring. The layers were separated and the aqueous layer was washed with methylene chloride. The combined organic layers were washed with water, dried and then concentrated to leave crude product. This material was chromatographed on 6–250 μ 8"×8" silica gel plates eluted twice with hexane: acetone (1:1). The center, major component was isolated and corresponded to the title compound. Faster and slower eluting components corresponded to bis-triflated product and starting material.

EXAMPLE 15

Preparation of
4-aza-4,7β-dimethyl-5α-androstan-3,17-dione

Step 1:

Synthesis of 3-Acetoxy-Androst-5-en-17-ol

To a solution of 100 mg (0.303 mmol) of 3-acetoxy-androst-5-en-17-one in 3 ml EtOH at −10° C., was added 22.9 mg (0.606 mmol) of sodium borohydride with stirring. After the reaction mixture was stirred for one and ½ hours, the mixture was diluted with 10 ml water, the ethanol solvent removed under vacuum, and the residue extracted with ethyl acetate. The organic layer was washed with aqueous $Na_2CO_3$, brine, dried over sodium sulfate and concentrated to leave a residue of crude title compound. The proton NMR was in accord with the assigned structure.

Step 2:

Synthesis of 3-Acetoxy-Androst-5-en-17-ol,
17-t-butyldimethyl-silyl ether

To a solution of the androstan-17-ol, from the previous synthesis, being 4.5 g (13.55 mmol) in 50 ml dimethylformamide at 23° C. was added 2.76 g (40–65 mmol) imidazole followed by 3.063 g (20.32 mmol) of t-butyldimethylsilyl chloride. The reaction mixture was stirred and a solid began to precipitate. Twenty additional ml of DMF were added and the mixture further stirred overnight. The mixture was poured into 1 liter water, the solid filtered and washed with water. The solid was dissolved in ethylacetate, the organic layer washed with brine and dried over sodium sulfate, concentrated to yield the silyl protected 17-ol title compound. The proton NMR was consistent with the assigned structure.

Step 3:

7-one-17β-ol, 17-t-butyldimethylsilyl ether

To a solution of the TBDMS protected 17-ol from the previous synthesis, being 5.6 g (12.55 mmol) in 100 ml acetonitrile at 23° C. was added 90% t-butyl hydrogen peroxide, 3.958 g (43.92 mol), and 138 mg chromium hexacarbonyl. After refluxing the mixture under nitrogen for 24 hours, the reaction mixture was poured into one liter water, solid was filtered, the residue washed with 500 ml water and the residue dissolved in 350 ml methylene chloride. The organic layer was washed with brine, dried over sodium sulfate and concentrated to yield crude material. Thin layer chromatography (3:1 hexane/ethyl acetate on silica gel) showed the presence of starting material. The solid was purified by column chromatography over silica gel by elution with 7% ethyl acetate/hexane to yield the title compound. The proton NMR was consistent with the assigned structure.

Step 4:

Synthesis of
3,7-dihydroxy-7-methyl-androst-5-en-17β-ol,
17-t-butyldimethylsilyl ether To a solution of the product from the previous synthesis, being 440 mg (0.956 mmol) in dry tetrahydrofuran at 0° C. was added dropwise methyl magnesium chloride over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield crude product. The proton NMR was consistent with the assigned structure of the title compound which was used in the next step without further purification.

Step 5:

Synthesis of
7-methyl-androst-4,6-dien-3-one-17β-ol,
17-t-butyldimethylsilyl ether The above Grignard product, 3.5 g (7.142 mmol) was dissolved in 50 ml toluene/50 ml cyclohexanone and 20 ml of solvent distilled off under vacuum. To this was added 4.54 g aluminum isopropoxide and the reaction mixture refluxed overnight for 15 hours. The mixture was cooled, diluted with ethyl acetate, washed with sodium potassium tartarate, brine, and the organic layer was concentrated under vacuum and the residue steam distilled. The residue was extracted with ethyl acetate, washed with brine, dried and purified by column chromatography on silica gel, eluting with 5% EtOAc/hexane to yield the title compound.

Step 6:

Synthesis of 7β-methyl-androst-5-en-3-one-17β-ol,
t-butyldimethylsilyl ether

To a solution of 370 mg of the product of the previous synthesis, in 5.5 ml ammonia, 1 ml THF, 1 ml toluene, was added 50 mg of metallic lithium in small pieces. After stirring the blue solution for 2 hours, a solution of 1,2-dibromomethane in 2 ml THF was added. After stirring the solution at −78° C. for 10 minutes, 250 mg of ammonium chloride was added and the mixture stirred for 10 minutes. The excess ammonia was removed by evaporation under a nitrogen steam. The reaction mixture was diluted with brine, extracted with ethyl acetate. The organic layer was washed with brine, dried and concentrated to yield crude material which was used as such in the next synthesis.

Step 7:

Synthesis of 7β-methyl-androst-4-en-3-on-17β-ol,
t-butyldimethylsilyl ether

To a solution of the product of the previous synthesis, being 432 mg in 4 ml THF was added 150 microliters DBU (1,8-diazabicyclo[5.4.0]undec-7-ene) under nitrogen with stirring. The mixture was refluxed for 1.5 hours, then cooled, diluted with $NH_4Cl$ solution. The solvent THF was removed under vacuum and the residue extracted with ethyl acetate. The organic layer was washed with brine, dried and concentrated under reduced pressure to yield crude material. The titled product was purified by chromatography on silica gel using 10% EtOAc/hexane as eluant.

Step 8:

Synthesis of
17β-(t-butyldimethylsilyloxy)-7β-methyl-5-oxo-A-nor-3,5-secoandrostan-3-oic acid To a solution of 884 mg of the product of the previous synthesis in 15 ml t-butyl alcohol at 80° C. was added 248 mg sodium carbonate in 1.5 ml water followed by a dropwise addition over 15–20 minutes of a mixture of 2.273 g sodium periodate with 16.8 mg potassium permanganate in 8 ml water. The reaction mixture was heated at 80° C. for 2 hours, cooled, filtered, the residue washed with water, and then the extract concentrated under vaccum. The extract was acidified with aqueous HCl, extracted with ethyl acetate and the organic layer washed with aqueous NaHSO₃, brine, dried and concentrated to yield crude 9. The proton NMR was consistent with the assigned structure.
Step 9:

Synthesis of
4,7β-dimethyl-4-aza-androst-5-en-3-one-17β-ol.
t-butyldimethylsilyl ether To a solution of the product of the previous synthesis, 840 mg in 5 ml ethylene glycol, was added 1.5 g sodium acetate and 737 mg methylamine hydrochloride. After stirring the reaction mixture 4 hours at 180° C., the mixture was cooled, diluted with water, extracted with ethyl acetate, dried and concentrated to afford crude title compound. The proton NMR was consistent with the assigned structure.
Step 10:

Synthesis of
4,7β-dimethyl-4-aza-androst-5-en-3-one-17β-ol

To a solution of 700 mg of the product of the previous example, in 20 ml of acetonitrile at 0° C., was added 500 microliters. aqueous HF. After stirring the reaction mixture for one hour, the HF was neutralized with aqueous sodium carbonate, diluted with water, acetonitrile removed under vacuum, and the residue extracted with ethyl acetate. The organic layer was dried, concentrated to give crude title compound which was further purified by preparative chromatography on silica gel using 3:1 chloroform/acetone.
Step 11:

Synthesis of
4,7β-dimethyl-4-aza-androstan-3-one-17β-ol

To a solution of the product of the previous synthesis, being 350 mg in 10 ml acetic acid was added 100 mg platinum dioxide and the resulting mixture was evacuated and flushed with hydrogen. The reaction was shaken overnight at room temperature under 40 Psig hydrogen pressure. The solution was filtered concentrated. The residue was worked up with ethyl acetate, the organic layer was then concentrated under vacuum, diluted with ethyl acetate, washed with aqueous NaHCO₃, brine, dried, concentrated to yield the title compound. Mass Spec: 320 (M+1).
Step 12:

Synthesis of
4-aza-4,7β-dimethyl-5α-androstan-3,17-dione

The product of the previous synthesis, 1.013 g (3.176 mmol) was placed with 6 ml methylene chloride into a dry flask. Powdered molecular 4 Å sieves, 1.6 g, and 0.558 g (4.76 mmol) of N-methylmorpholine-N-oxide (NMO) and then tetrapropylammonium perruthenate (TPAP), 55 mg (0.159 mmol) were added. The reaction was stirred for 2 hours, diluted with 150 ml ethyl acetate and filtered. The filtrate was evaporated to dryness to yield crude product which was recrystallized from EtOAc to yield pure product, mp 135°–138° C.

Elemental Analysis Calc'd for C₂₀H₃₁NO₂, mw=317.48 Calc'd: C, 75.67; H, 9.84; N, 4.41 Found: C, 75.16; H, 10.22; N, 4.13 Mass Spec. 318 (M+1).

EXAMPLE 16

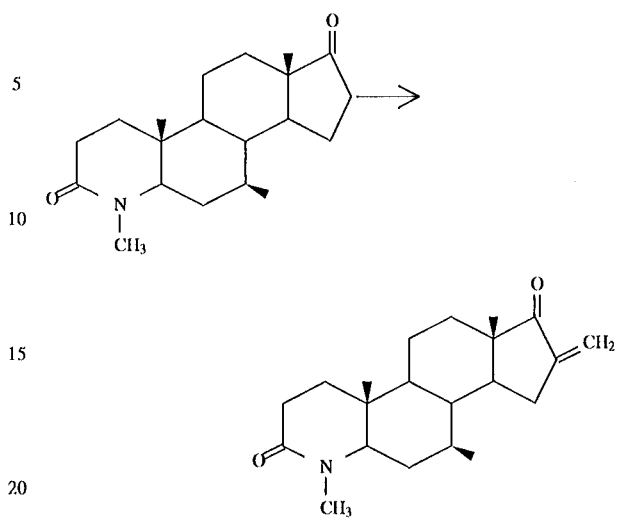

Step 1:

Synthesis of
16-methylene-4,7β-dimethyl-4-aza-5α-androstan-3,17-dione

To a solution of 4-aza-4,7β-dimethyl-5α-androstan-3,17-dione (1 g, 3.15 mmol) in DMSO (dimethyl sulfoxide) (20 ml) was added N-methylanilinium trifluoroacetate (2.088 g, 9.45 mmol) and paraformaldehyde (850 mg, 28.35 mmol). After stirring the reaction mixture for 2 hrs at 110° (bath temperature), the reaction mixture was cooled and additional N-methylanilinium trifluoroacetate (2.088 g, 9.45 mmol) and paraformaldehyde (850 mg, 28.35 mmol) was added and reaction stirred further for 2 hrs at 110° C. The reaction mixture was cooled and N-methylanilinium trifluoroacetate (1.044 g, 4.72 mmol) and paraformaldehyde (425 mg, 14.16 mmol) was added and after stirring the reaction mixture for 2 hrs at 110°, the reaction mixture was cooled, diluted with water and extracted with ethyl acetate. The organic layer was washed with brine, dried and concentrated. The residue was purified by column chromatography over silica gel using 10% acetone/methylene chloride as solvent to give the title product. ¹H NMR (400 MHz, CDCl₃, ppm, Key peaks) 0.88 and 0.91 ( C-18, C-19), 1.1 (d, C-7), 2.92 (4N-CH₃), 3.05 (dd, C-5),5.39 and 6.08 (16-CH₂).

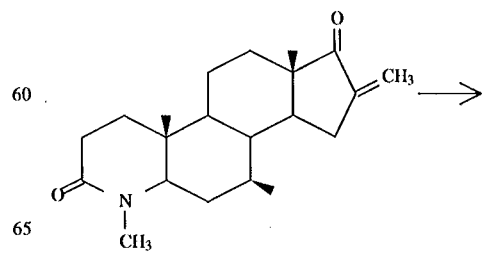

-continued

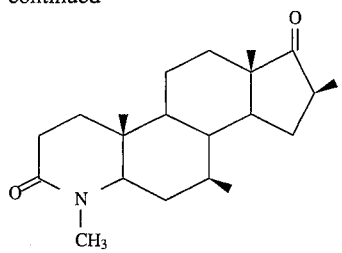

Step 2:

Synthesis of
4,7β,16β-trimethyl-4-aza-5α-androstan- 3, 17-dione

To a solution of 16-methylene-4,7β-dimethyl-4-aza-5α-androstan- 3,17-dione (925 mg, 2.81 mmol added 10% Pd/C (100 mg). The reaction mixture was evacuated and flushed with hydrogen (3 times). After stirring the reaction mixture overnight at room temperature, the reaction was flushed with nitrogen and filtered. The residue was washed with methanol and combined organic extract was concentrated under vacuum to give the title product. $^1$H NMR (400 MHz, CDCl$_3$, ppm, Key peaks) 0.84 and 0.86 (C-18 and C-19), 1.11 (d, C-7), 1.18 (d, C-16), 2.92 (4N-Me), 3.04 (dd, C-5).

EXAMPLE 17

Preparation of
4,7β-dimethyl-17-(3-methoxyphenyl)-4-aza-
5α-androstan- 3-one 4,7β-Dimethyl-17-(3-methoxyphenyl)-4-aza-5α-androst-16-en-3-one (32.7 mg, 0.08 mmol) was dissolved in ethanol (3 ml) with 10% palladium on activated carbon (4.7 mg, 15% by wt.). The flask was purged three times, vacuum versus hydrogen, and stirred vigorously under slight hydrogen pressure at room temperature until starting material was consumed. (Hydrogen pressure was maintained by an attached balloon.) Progress of the reduction was monitored by HPLC on an E. Merck 5μ RP-18 column, eluting with CH$_3$CN:THF:H$_2$O (85:5:10). The reaction was complete in 2 hrs. The solution was filtered through celite and reduced in vacuo. The product was isolated by crystallization from ether to give the title compound.

Employing the procedures substantially as described in the foregoing examples, the following compounds shown in Tables I and II were synthesized. The compounds of Table III are intermediates used in the preparation of compounds of this invention. "Me" stands for methyl; "Ph" stands for phenyl; "Et" stands for ethyl; "Ac" stands for CH$_3$C(O)—.

Proton nuclear magnetic resononance (NMR) spectra were done at 400 MHz, ambient temperature, in CDCl$_3$ except for compounds denoted with an asterisk, for which D$_6$-acetone was used. Peak values are given in ppm. "Ene" represents a double bond at the C16–C17 position, and "ane" represents a single bond.

TABLE I

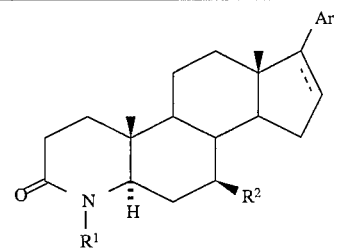

| R$^1$ | R$^2$ | 16, 17 | Ar | m.p. (°C.) |
|---|---|---|---|---|
| Me | H | ene | phenyl | |
| H | H | ane | phenyl | |
| Me | H | ane | phenyl | |
| Me | H | ene | 4-hydroxymethyl-phenyl | oil |
| Me | H | ene | 4-methyl phenyl | 214–215 |
| Me | H | ane | 4-methyl phenyl | 208–209 |
| Me | H | ene | 4-methoxy phenyl | 200–201 |
| Me | H | ane | 4-methoxy phenyl | 189.5–190 |
| Me | H | ene | 4-methylthio phenyl | 198–199 |
| Me | H | ane | 4-methylthio phenyl | 175–176 |
| Me | Me | ane | 4-methylthio phenyl | |
| Me | H | ene | 4-formyl phenyl | 210–211 |
| Me | Me | ene | phenyl | oil |
| Me | Me | ane | phenyl | 145–146 |
| Me | H | ene | 4-chloro phenyl | 195–196 |
| Me | H | ane | 4-chloro phenyl | 208–209 |
| Me | Me | ene | 4-chloro phenyl | 156–157 |
| Me | Me | ane | 4-chloro phenyl | oil |
| Me | H | ene | 2-methyl phenyl | 168–169 |
| Me | H | ane | 2-methyl phenyl | 198–199 |
| Me | H | ene | 3-methyl phenyl | 195–196 |
| Me | H | ane | 3-methyl phenyl | 163–164 |
| Me | H | ene | 2-methoxy phenyl | 145–146 |
| Me | H | ane | 2-methoxy phenyl | 174–175 |
| Me | H | ene | 3-methoxy phenyl | 188–189 |
| Me | H | ane | 3-methoxy phenyl | 152–153 |
| Me | Me | ene | 3,5-bis-(trifluoromethyl)phenyl | 126–127 |
| Me | Me | ane | 3,5-bis-(trifluoromethyl)phenyl | oil |
| Me | Me | ene | 1-naphthyl | 157–158 |
| Me | Me | ene | 3,5-dichloro phenyl | |
| Me | Me | ane | 3,5-dichloro phenyl | |
| Me | Me | ene | 2,4-dichloro phenyl | |
| Me | Me | ane | 1-naphthyl | 196–197 |
| Me | Me | ane | 2-methoxy phenyl | oil |
| Me | Me | ane | 3-methoxy phenyl | |
| Me | Me | ene | 4-methoxy phenyl | |
| Me | Me | ane | 4-methoxy phenyl | |
| Me | Me | ene | 4-methylsulfonyl phenyl | |
| Me | Me | ane | 4-methylsulfonyl phenyl | |
| Me | Me | ane | 3-amino phenyl | |
| Me | Me | ane | 3-(carbethoxyamino)-phenyl | |

TABLE II

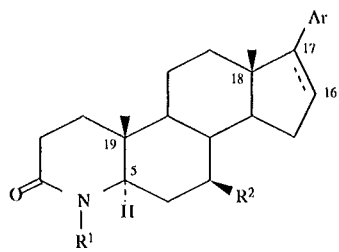

NMR VALUES
(PPM, CDCl₃ OR D₆-ACETONE AS NOTED)

| 16-17 | R¹ | R² | Ar | C18-Me | C19-Me | C17α-H | C5α-H | Other |
|---|---|---|---|---|---|---|---|---|
| ane | H | H | Ph | 0.45 | 0.86 | 2.66t | 3.06 dd | |
| ane | Me | H | Ph | 0.45 | 0.85 | 2.66t | 3.03 dd | 2.91 s, 4-Me |
| ene | Me | Me | Ph | 1.02 | 0.88 | . . | 3.05 dd | 1.08 d, 7-Me<br>5.86 nm, 16-H |
| ane | Me | Me | β-Ph | 0.46 | 0.82 | 2.58t | 3.04 dd | 1.07 d, 7-Me |
| ene | Me | H | 4-CH₂OH—Ph | 1.01 | 0.90 | . . | 3.00 dd | 5.99 ndd, 16-H<br>4.64 s, CH₂O |
| ene | Me | H | 4-CHO—Ph | 1.05 | 0.92 | . . | 3.05 dd | 6.08 nm, 16-H<br>9.95 s, CHO |
| ene | Me | H | 4-Me—Ph | 1.00 | 0.92 | . . | 3.05 dd | 5.83 ndd, 16-H<br>2.31 s, Ar—Me |
| ane | Me | H | 4-Me—Ph | 0.44 | 0.85 | 2.63t | 3.03 dd | 2.30 s, Ar—Me<br>7.07 s, (4H) Ar |
| ene | Me | H | 2-Me—Ph | 0.91 | 0.91 | . . | 3.06 dd | 2.27 s, Ar—Me<br>5.55 nm, 16-H |
| ane | Me | H | 2-Me—Ph | 0.62 | 0.89 | 3.08t | 3.05 m | 2.33 s, Ar—Ph<br>2.93 s, 4Me |
| ene | Me | H | 3-Me—Ph | 1.01 | 0.92 | . . | 3.05 dd | 2.33 s, Ar—Me<br>5.87 nm, 16-H |
| ane | Me | H | 3-Me—Ph | 0.47 | 0.86 | 2.62t | 3.04 dd | 2.31 s, Ar—Me |
| ene | Me | H | 4-OMe—Ph | 0.99 | 0.92 | . . | 3.05 dd | 5.78 ndd, 16-H<br>3.78 s, Ar—OMe |
| ene | Me | Me | 4-OMe—Ph | 1.00 | 0.87 | . . | 3.05 dd | 5.76 dd, 16-H,<br>1.07 d, 7-Me<br>6.81–7.25 ABq |
| ane | Me | H | 4-OMe—Ph | 0.44 | 0.85 | 2.60t | 3.03 dd | 3.77 s, Ar—OMe<br>6.81 d, 7.09 d |
| ane | Me | Me | 4-OMe—Ph | 0.49 | 0.84 | 2.57t | 3.10 dd | 1.1 d, 7-Me<br>6.83–7.14 ABq |
| ene | Me | H | 2-OMe—Ph | 0.90 | 0.89 | . . | 3.05 dd | 5.76 nm, 16-H<br>3.78 s, Ar—OMe |
| ane | Me | H | 2-OMe—Ph | 0.51 | 0.88 | 3.31t | 3.03 dd | 3.75 s, Ar—OMe |
| ene | Me | Me | 2-OMe—Ph | 0.90 | 0.87 | . . | 3.08 dd | 5.71 nm, 16-H<br>1.08 d, 7-Me |
| ane | Me | Me | 2-OMe—Ph | 0.53 | 0.82 | 3.26t | 3.05 dd | 3.75 s, Ar—OMe<br>1.07 d, 7-Me |
| ene | Me | H | 3-OMe—Ph | 1.01 | 0.92 | . . | 3.06 dd | 5.89 nm, 16Me<br>3.78 s, Ar—OMe |
| *ene | Me | Me | 3-OMe—Ph | 1.06 | 0.90 | . . | 3.11 dd | 3.78 s, Ar—OMe<br>5.92 t, 16-H<br>1.11 d, 7-Me |
| ane | Me | H | 3-OMe—Ph | 0.46 | 0.86 | 2.64t | 3.04 dd | 3.79 s, Ar—OMe |
| *ane | Me | Me | 3-OMe—Ph | 0.52 | 0.84 | 2.61t | 3.11 dd | 3.76 s, Ar—OMe<br>1.10 d, 7-Me |
| ene | Me | H | 4-SMe—Ph | 1.00 | 0.92 | . . | 3.05 dd | 2.92 s, Ar—SMe<br>7.20, 7.26 d |
| ene | Me | Me | 4-SMe—Ph | 1.01 | 0.88 | . . | 3.05 dd | 2.92 s, Ar—SMe<br>5.85 t, 16-H<br>1.08 d, 7-Me<br>7.16–7.25 ABq |
| ane | Me | H | 4-SMe—Ph | 0.44 | 0.85 | 2.61t | 3.03 dd | 2.91 s, Ar—SMe<br>7.11 d, 7.15 d |
| ane | Me | Me | 4-SMe-Ph | 0.46 | 0.82 | 2.54t | 3.04 dd | 2.44 s, Ar—SMe<br>1.08 d, 7-Me<br>7.08–7.16 ABq |
| ene | Me | Me | 4-SO₂Me—Ph | 1.05 | 0.88 | . . | 3.06 dd | 6.05 m, 16-H<br>3.03 s, SO₂Me<br>1.18 d, 7-Me<br>7.49–7.82 ABq |
| ane | Me | Me | 4-SO₂Me—Ph | 0.47 | 0.83 | 2.68t | 3.09 dd | 3.04 s, SO₂Me<br>1.09 d, 7-Me |
| *ene | Me | Me | 4-CN—Ph | 1.13 | 0.91 | . . | 3.13 dd | 1.12 d, 7-Me |

TABLE II-continued

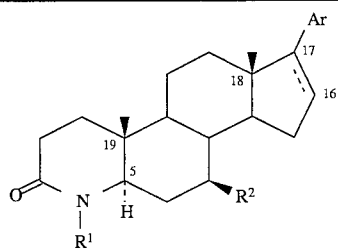

NMR VALUES
(PPM, CDCL₃ OR D₆-ACETONE AS NOTED)

| 16-17 | R¹ | R² | Ar | C18-Me | C19-Me | C17α-H | C5α-H | Other |
|---|---|---|---|---|---|---|---|---|
| *ane | Me | Me | 4-CN—Ph | 0.52 | 0.84 | 2.76t | 3.12 dd | 7.59–7.69 ABq<br>1.11 d, 7-Me |
| ene | Me | H | 4-Cl—Ph | 0.99 | 0.92 | — | 3.08 dd | 7.46–7.68 ABq<br>5.89 nm, 16-H |
| ane | Me | H | 4-Cl—Ph | 0.42 | 0.86 | 2.62t | 3.03 dd | 7.25 ndd, (4H) Ar<br>7.10 d, 7.22 d |
| ene | Me | Me | 4-Cl—Ph | 1.00 | 0.89 | — | 3.05 dd | 5.88 nm, 16-H<br>7.24 s, (4H) Ar |
| ane | Me | Me | 4-Cl—Ph | 0.47 | 0.84 | 2.58t | 3.05 dd | 1.09 d, 7-Me<br>7.08 d, 7.21 d |
| ene | Me | Me | 2,4-Cl₂—Ph | 0.89 | 0.86 | — | 3.05 dd | 5.70 t, 16-H<br>1.08 d, 7-Me |
| ane | Me | Me | 2,4-Cl₂—Ph | 0.57 | 0.82 | 3.28t | 3.03 dd | 1.07 d, 7-Me |
| *ene | Me | Me | 3,5-Cl₂—Ph | 1.07 | 0.91 | — | 3.13 dd | 6.13 dd, 16-H<br>1.11 d, 7-Me |
| *ane | Me | Me | 3,5-Cl₂—Ph | 0.54 | 0.85 | 2.69t | 3.12 dd | 1.10 d, 7-Me |
| ene | Me | Me | 3,5(CF₃)₂—Ph | 1.04 | 0.89 | — | 3.08 dd | 6.06 nt, 16-H<br>1.10 d, 7-Me |
| ane | Me | Me | 3,5(CF₃)₂—Ph | 0.46 | 0.82 | 2.71t | 3.04 dd | 1.08 d, 7-Me<br>7.59 s(2H), ArH |
| *ane | Me | Me | 3-NH₂—Ph | 0.52 | 0.84 | 2.48t | 3.11 dd | 1.10 d, 7-Me |
| *ane | Me | Me | 3-NHAc—Ph | 0.51 | 0.84 | 2.59t | 3.12 dd | 2.05 s, NH—Ac<br>1.09 d, 7-Me |
| *ane | Me | Me | 3-NHCO₂Et—Ph | 0.52 | 0.85 | 2.61t | 3.11 dd | 4.15 q, 1.23 t,<br>NHCO₂Et<br>1.11 d, 7-Me |
| ene | Me | Me | 1-naphthyl | 0.99 | 0.86 | — | 3.08 dd | 5.73 t, 16-H<br>1.14 d, 7-Me |
| ane | Me | Me | 1-naphthyl | 0.61 | 0.91 | 3.69t | 3.08 dd | 1.12 d, 7-Me |
| ane | H | Me | 4-OMe—Ph | 0.446 | 0.836 | 2.54 | 3.09 dd | 6.81, 7.10 d<br>1.045 d, 7-Me |
| † ane | H | Me | 4-OMe—Ph | 0.48 | 0.90 | 2.55 | 3.37 dd | 5.51 dd, (Δ1), 6.80,<br>(Δ1), 6.83 d, 7.11<br>(AR) |
| ane | H | Me | 4-SMe—Ph | 0.46 | 0.835 | 2.54 | 3.09 dd | 2.45 (SMe), 7.09 d,<br>7.16 d (AR) |
| † ane | H | Me | 4-SMe—Ph | 0.477 | 0.89 | 2.56 | 3.35 dd | 2.45 (SMe), 5.79 dd<br>(Δ1), 6.79 d (Δ1),<br>7.1 d, 7.19 d (AR) |

† Compound has C1-C2 double bond (Δ1)

TABLE III

[Structure diagram of steroid with Ar at C17, R³ at C16, R² at C7, N-R¹ ring A, positions 5, 18, 19 labeled]

NMR VALUES (PPM, CDCl₃)

| 16-17 | R¹ | R² | R³ | X | C18-Me | C19-Me | C17α-H | C5α-H | Other |
|---|---|---|---|---|---|---|---|---|---|
| ene | H | H | H | O₃SCF₃ | 0.96 | 0.92 | - - | 3.06 dd | 5.56 nm, 16-H |
| ene | H | Me | H | O₃SCF₃ | 0.95 | 0.87 | - - | 3.09 dd | 1.00 d, 7-Me 5.54 nm, 16-H |
| ene | Me | Me | H | O₃SCF₃ | 0.96 | 0.86 | - - | 3.05 dd | 5.55 nm, 16-H 1.03 d, 7-Me |
| ene | Me | H | H | O₃SCF₃ | 0.95 | 0.89 | - - | 3.03 dd | 5.55 nm, 16-H |
| ane | H | H | H | β-OH; α-Ph | 1.04 | 0.85 | - - | 2.91 dd | |
| ane | Me | Me | =CH₂ | C=O | 0.88 | 0.91 | - - | 3.05 dd | 2.92 (4N—Me), 5.39 and 6.08 (16-CH₂) |
| ane | Me | Me | Me | C=O | 0.84 | 0.86 | - - | 3.04 dd | 2.92 (4N—Me), 1.11 (d, C-7), 1.18(d, C-16) |
| ene | Me | H | Me | O₃SCF₃ | 0.88 | 0.93 | - - | 3.05 dd | 1.70 (16-Me), 2.91 (4N—Me) |

Biological Assays preparation of Human Prostatic and Scalp 5α-Reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-Reductase Assay

The reaction mixture for the type 1 5α-reductase contained 40 mM potassium phosphate, pH 6.5, 5 mM [7-³H]-testosterone, 1 mM dithiothreitol and 500 μM NADPH in a final volume of 100 μl. The reaction mixture for the type 2 5α-reductase contained 40 mM sodium citrate, pH 5.5, 0.3 mM [7-³H]-testosterone, 1 mM dithiothreitol and 500 μM NADPH in a final volume of 100 μl. Typically, the assay was initiated by the addition of 50–100 μg prostatic homogenate or 75–200 μg scalp homogenate and incubated at 37° C. After 10–50 min the s reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman panisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655α autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. The compound to be tested was pre-incubated with the enzyme (either 5α-reductase type 1 or 2) prior to initiation by addition of substrate testosterone. IC₅₀ values represent the concentration of inhibitor required to decrease enzyme conversion of testosterone to dihydrotestosterone by 50% of the control. IC₅₀ values were determined using a 6 point titration where the concentration of the inhibitor was varied from 0.1 to 1000 nM. Representative compounds of this invention were tested in the above described assay for 5α-reductase type 1 and type 2 inhibition.

A compound referred to herein as a 5α-reductase 2 inhibitor is a compound that shows inhibition of the 5α-reductase 2 isozyme in the above-described assay, having an IC₅₀ value of about or under 100 nM.

The compounds described in Tables I and II were tested in the above-described assay for 5α-reductase type 1 and type 2 inhibition, and were found to have IC₅₀ values under about 100 nM for inhibition of the type 1 isozyme. Compounds in Tables I and II within the scope of formula II were found to have IC₅₀ values of under about 50 nM for inhibition of the type 1 isozyme. Tested compounds of this invention that showed dual inhibitory activity additionally had IC₅₀'s under about 200 nM for inhibition of the type 2 isozyme.

The tested compounds within the scope of formula II were at least about 5 times more active in the type 1 5α-reductase assay than in the type 2 assay, with the majority being at least 10 times more active in the type 1 assay, thereby demonstrating their utility as selective type 1 inhibitors. The majority of tested compounds within the scope of formula IV were at least about 5 times more active in the type 1 assay than in the type 2 assay.

Human Dermal Papilla Cell Assay

The dermal papilla is a small group of cells at the base of each hair follicle, and it is presently thought that these cells are stem cells that form the basis for hair growth. These cells have been shown to have 5 alpha reductase activity, and it is therefore possible to test inhibitors of 5 alpha reductase in these cell culture systems.

Isolated and cultured dermal papilla cells are prepared according to the methods of Messenger, A. G., "The Culture of Dermal Papilla Cells From Human Hair Follicles," *Br. J. Dermatol.*, 110:685–689 (1984) and Itami, S. et al., "5α-Reductase Activity In Cultured Human Dermal Papilla Cells From Beard Compared With Reticular Dermal Fibroblasts," *J. Invest. Dermatol.*, 94:150–152 (1990). Beard dermal papilla cells and occipital scalp hair of two different individuals are used throughout the study. All experiments are performed at confluency after the fourth to sixth subculture. Confluent monolayers are rinsed twice with phosphate-buffered saline, scraped from dishes by rubber policemen, and collected into a centrifuge tube. The cell suspensions are centrifuged at 1,500 rpm for 10 min at 4° C. The pellets are resuspended in 20 mM Tris-HCl buffer, pH 7.5, at 4° C., containing 250 mM sucrose, 1 mM $MgCl_{12}$, and 2 mM $CaCl_2$, by vortexing and 10 passes through a 25-gauge needle. The crude homogenate is further homogenized by a teflon-glass homogenizer, and is used as the cell homogenate. For the study of subcellular localization of 5α-reductase, the cell homogenate is centrifuged at 800×g for 10 min to yield a crude nuclear pellet. The resultant supernatant is centrifuged at 10,000×g for 15 min to produce a crude mitochondrial pellet. The supernatant is centrifuged at 100,000×g for 60 min to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 ml of the cell homogenate, in a final volume of 100 ml. Each tube contains 50–100 mg of cellular protein. Incubation is carried out at 37° C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et al., "Protein Measurement With The Folin Phenol Reagent," *J. Biol. Chem.*, 193:265–275 (1951).

After incubation, the reaction is stopped by adding 4 times volume of chloroform-methanol (2/1:V/V) containing 110 mg each of carrier steroids. The extracted steroids are analyzed by thin-layer chromatography as previously described by Gomez, et al., "In Vitro Metabolism Of Testosterone-4-$^{14}$C and D-androstene-3, 17-dione- 4-$^{14}$C In Human Skin," *Biochem.*, 7:24–32 (1968), and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

The following describes an example of methodology that can be used for detection of hair growth.

MACROPHOTOGRAPHY AND GLOBAL PHOTOGRAPHY PROCEDURE FOR DETECTION OF HAIR GROWTH

A. Macrophotographic Procedure

Location: ID card Haircount target area

Equipment: Film: Kodak-T-max 24 exposure each of same emulsion lot number

Camera: Nikon N-6000

Lens: Nikkor 60 mm f2.8

Flashes: Nikon SB-21B Macroflash

Device: registration device

Photographic Procedure:

In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly anterior to the center of the vertex bald spot, using a commercial tattooing machine or manually (needle and ink). An area approximately one square inch in size, centered at the tattoo at the leading edge of the balding area, is clipped short (~2 mm). Cut hairs are removed from the area to be photographed, using tape. Compressed air and/or ethanol wipes may also be used to facilitate removal of cut hairs.

2. Magnification: Each lens supplied has a fixed reproduction ratio of 1:1.2. Aperture: Every photograph is taken at f/22. Film: T-Max 100 (24 exposure) is used.

3. Patient's haircount target area. Three exposures (−2/3, 0, and +2/3 f-stop).

A trained technician places a transparency over the photographic print and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and DeLong, E., *J. American Academy of Dermatology*, Vol. 23, p. 470 (1990).

B. Global Photographic Procedure

Locations: Color card/patient Id Global photograph

Equipment: Film: Kodachrome KR-64 24 exposure each of same emulsion lot number

Camera: Nikon N-6000

Lens: Nikkor 60 mm f2.8

Flashes: Nikon SB-23

Photographic Procedure

In these clinical photographs, the only variable allowed is the global area's appearance. Anything extraneous to the area (clothing, furniture, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.

2. Magnification: Each lens supplied has a fixed reproduction ratio of 1:6. Aperture: Every photograph will be taken at f/11. Film: Kodachrome (24 exposure) is used.

3. Patient's global photographs. Three exposures at zero compensation.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I

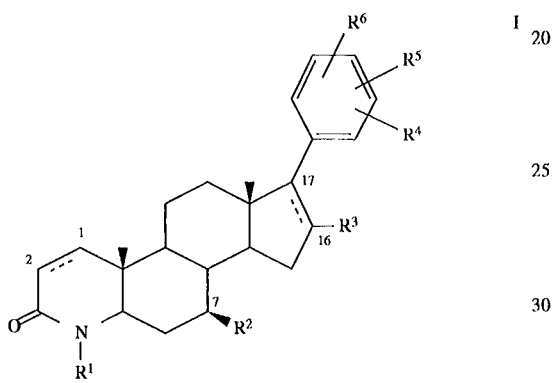

or a pharmaceutically acceptable salt or ester thereof, wherein: the C1–C2 bond and the C16–C17 bond designated "———" each independently represent a single or double bond;

$R^1$ and $R^2$ are independently selected from:
1) —H,
2) —$CH_3$ and
3) —$CH_2CH_3$;

$R^3$ is selected from:
1) —H and
2) —$CH_3$; and $R^3$ is β-oriented if C16—C17 is saturated;

$R^4$, $R^5$ and $R^6$ are independently selected from:
1) —H,
2) —$C_{1-8}$ alkyl, unsubstituted or substituted with a single —OH substituent,
3) —$C_{1-3}$ perfluoroalkyl,
4) —halo,
5) —$OR^7$, wherein $R^7$ is
   a) —H,
   b) —$C_{1-8}$ alkyl,
   c) —$C_{1-6}$ alkylcarbonyl,
   d) —$C_{1-6}$ alkylsulfonyl, or
   e) —$C_{1-6}$ alkoxycarbonyl,
6) —$NHR^7$,
7) —$NO_2$,
8) —$S(C_{1-6}$ alkylcarbonyl),
9) —$S(O)_nC_{1-8}$ alkyl, wherein n is 0, 1 or 2,
10) —$CO_2R^8$ wherein $R^8$ is
    a) —H or
    b) —$C_{1-8}$ alkyl,
11) —$C(O)R^8$,
12) —$C(O)N(R^8)_2$,
13) —CN,
14) —$C(R^8)_2OR^7$,
15) —$C(R^8)_2NR^7$,
16) —$C(R^8)_2S(C_{1-8}$ alkyl),
17) —$C(R^8)_2S(C_{1-6}$ alkylcarbonyl), and
18) phenyl, unsubstituted or having 1 to 3 substituents selected from:
    a) —OH,
    b) halo,
    c) $C_{1-3}$ alkyl, and
    d) $C_{1-3}$ alkoxy; or $R^4$ and $R^5$ or $R^5$ and $R^6$, on vicinal carbon atoms, may be joined to form with the phenyl to which they are attached a naphthyl or indanyl group; and the 17-position substituent is β-oriented if C16–C17 is saturated.

2. The compound of claim 1 of the formula II:

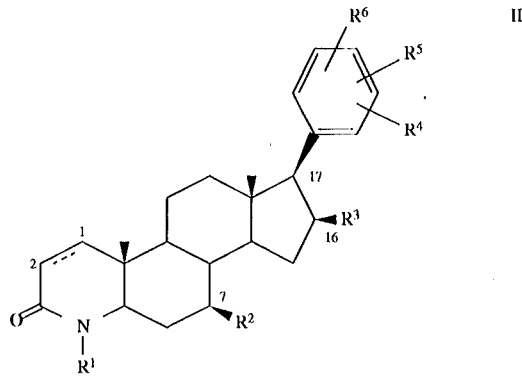

3. The compound of claim 2 of the formula III

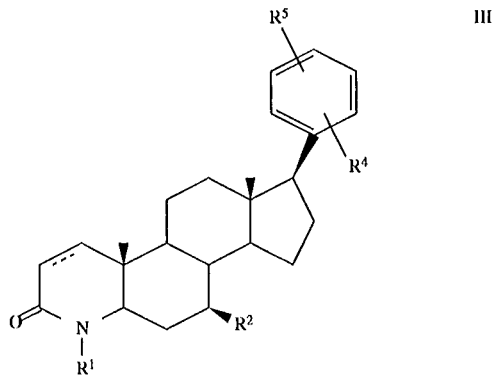

or a pharmaceutically acceptable salt or ester thereof, wherein:
$R^1$ is —H, or —$CH_3$; and
$R^2$ is —$CH_3$ or —$CH_2CH_3$.

4. The compound of claim 3 wherein:
$R^1$ is —H or —$CH_3$;
$R^2$ is —$CH_3$; and
$R^4$ and $R^5$ are independently selected from
a) —H,
b) —OH,
c) —$CH_3$,
d) —$OCH_3$,
e) —$S(O)_n$—$CH_3$,
f) —$CF_3$,
g) halo,
h) —CHO,
i) CN,
j) —$NHR^7$, or 5,525,608

R⁴ and R⁵ are on vicinal carbon atoms and are joined to form with the phenyl to which they are attached a naphthyl group.

5. The compound of claim 3 wherein:

the C1–C2 bond is a single bond;

R¹ is —H or —CH₃; and

R² is —CH₃.

6. The compound of claim 5 wherein R⁴ and R⁵ are independently selected from:

a) —H,
b) —OH,
c) —CH₃,
d) —OCH₃,
e) —S(O)ₙ—CH₃,
f) —CF₃,
g) halo,
h) —CHO,
i) CN,
j) —NHR⁷, or R⁴ and R⁵ are on vicinal carbon atoms and are joined to form with the phenyl to which they are attached a naphthyl group.

7. The compound of claim 6 selected from the group in the following table:

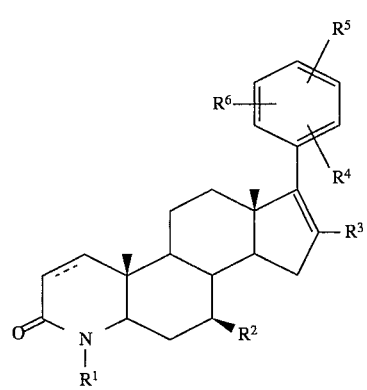

| R¹ | R² |  |
|---|---|---|
| —CH₃ | —CH₃ | phenyl |
| —CH₃ | —CH₃ | 4-methylthiophenyl |
| —CH₃ | —CH₃ | 4-chlorophenyl |
| —CH₃ | —CH₃ | 3,5-bis(trifluoromethyl)-phenyl |
| —CH₃ | —CH₃ | 3,5-dichlorophenyl |
| —CH₃ | —CH₃ | 1-naphthyl |
| —CH₃ | —CH₃ | 2-methoxyphenyl |
| —CH₃ | —CH₃ | 3-methoxyphenyl |
| —CH₃ | —CH₃ | 4-methoxyphenyl |
| —CH₃ | —CH₃ | 4-methylsulfonylphenyl |
| —CH₃ | —CH₃ | 3-aminophenyl |
| —CH₃ | —CH₃ | 3-(carbethoxyamino)-phenyl. |

8. The compound of claim 1 of the formula IV

IV or a pharmaceutically acceptable salt or ester thereof.

9. The compound of claim 8 of the formula V:

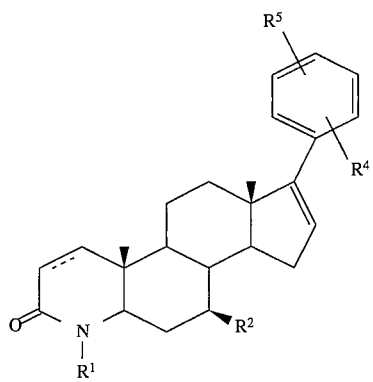

V or a pharmaceutically acceptable salt or ester thereof wherein:

R¹ is —H or —CH₃; and

R² is —CH₃ or —CH₂CH₃.

10. The compound of claim 9 wherein:

R¹ is —H or —CH₃;

R² is —CH₃; and

R⁴ and R⁵ are independently selected from:

a) —H,
b) —OH,
c) —CH₃,
d) —OCH₃,
e) —S(O)ₙ—CH₃,
f) —CF₃,
g) halo,
h) —CHO,
i) CN,
j) —NHR⁷, or R⁴ and R⁵ are on vicinal carbon atoms and are joined to form with the phenyl to which they are attached a naphthyl group.

11. The compound of claim 9 wherein:

the C1–C2 bond is a single bond;

R¹ is —H or —CH₃; and

R² is —CH₃.

12. The compound of claim 11 wherein:

R⁴ and R⁵ are independently selected from:

a) —H,
b) —OH,
c) —CH₃,
d) —OCH₃,
e) —S(O)ₙ—CH₃,
f) —CF₃,
g) halo,
h) —CHO,
i) CN,
j) —NHR⁷, or R⁴ and R⁵ are on vicinal carbon atoms and are joined to form with the phenyl to which they are attached a naphthyl group.

13. The compound of claim 12 selected from the group in the following table:

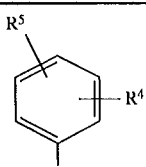

| $R^1$ | $R^2$ |  |
|---|---|---|
| —CH₃ | —CH₃ | phenyl |
| —CH₃ | —CH₃ | 4-methylthiophenyl |
| —CH₃ | —CH₃ | 4-chlorophenyl |
| —CH₃ | —CH₃ | 3,5-bis(trifluoromethyl)-phenyl |
| —CH₃ | —CH₃ | 3,5-dichlorophenyl |
| —CH₃ | —CH₃ | 1-naphthyl |
| —CH₃ | —CH₃ | 2-methoxyphenyl |
| —CH₃ | —CH₃ | 3-methoxyphenyl |
| —CH₃ | —CH₃ | 4-methoxyphenyl |
| —CH₃ | —CH₃ | 4-methylsulfonylphenyl |
| —CH₃ | —CH₃ | 3-aminophenyl |
| —CH₃ | —CH₃ | 3-(carbethoxyamino)-phenyl. |

14. A method for treating acne vulgaris comprising the step of administering to a human in need of such treatment a therapeutically effective amount of a compound of claim 1.

15. A method for treating acne vulgaris comprising the step of administering to a human in need of such treatment a therapeutically effective amount of a compound of claim 1 in combination with an inhibitor of 5α-reductase 2.

16. The method of claim 15 wherein the inhibitor of 5α-reductase 2 is finasteride.

17. A method for treating acne vulgaris comprising administering to a human patient in need of such treatment a therapeutically effective amount of a compound of claim 1 in combination with a retinoic acid or an ester or amide derivative thereof.

18. A pharmaceutical composition for the treatment of acne vulgaris comprising a pharmaceutically acceptable carrier and a therapeutically effective amount of a compound of claim 1.

19. The pharmaceutical composition of claim 18 further comprising a therapeutically effective amount of an inhibitor of 5α-reductase 2.

20. The composition of claim 19 wherein the 5α-reductase 2 inhibitor is finasteride, or a pharmaceutically acceptable salt thereof.

21. The pharmaceutical composition of claim 18 further comprising a therapeutically effective amount of retinoic acid or an ester or amide derivative thereof.

22. A pharmaceutical composition for the treatment of acne vulgaris comprising a pharmaceutically acceptable carrier adapted for topical application and a therapeutically effective amount of a compound of claim 1.

23. The pharmaceutical composition of claim 22 further comprising a therapeutically effective amount of a compound selected from finasteride, and retinoic acid or an ester or amide derivative thereof, or a pharmaceutically acceptable salt thereof.

24. A pharmaceutical composition for the treatment of acne vulgaris comprising a pharmaceutically acceptable carrier adapted for oral administration and a therapeutically effective amount of a compound of claim 1.

25. The pharmaceutical composition of claim 24 further comprising a therapeutically effective amount of finasteride or a pharmaceutically acceptable salt thereof.

* * * * *

UNITED STATES PATENT AND TRADEMARK OFFICE
CERTIFICATE OF CORRECTION

PATENT NO.   : 5,525,608

DATED        : June 11, 1996

INVENTOR(S)  : ALAN D. ADAMS et al.

It is certified that error appears in the above-identified patent and that said Letters Patent is hereby corrected as shown below:

In Claim 1, Column 37, line 36, delete "_____", and insert "--------" therefor.

Signed and Sealed this

Twentieth Day of August, 1996

Attest:

BRUCE LEHMAN

*Attesting Officer*    *Commissioner of Patents and Trademarks*